US010258607B2

(12) United States Patent
Gillies et al.

(10) Patent No.: US 10,258,607 B2
(45) Date of Patent: Apr. 16, 2019

(54) METHOD OF INCREASING INTRATUMORAL PHE AND REDUCING ACID-MEDIATED INVASION

(75) Inventors: Robert J. Gillies, Tampa, FL (US); David L. Morse, Tampa, FL (US); Ariosto Siqueira Silva, Tampa, FL (US); Arig A. Ibrahim Hashim, Tampa, FL (US); Robert A. Gatenby, Tampa, FL (US); Gary Martinez, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 301 days.

(21) Appl. No.: 13/479,638

(22) Filed: May 24, 2012

(65) Prior Publication Data

US 2012/0277245 A1 Nov. 1, 2012

Related U.S. Application Data

(63) Continuation of application No. PCT/US2010/057991, filed on Nov. 24, 2010.

(60) Provisional application No. 61/263,971, filed on Nov. 24, 2009.

(51) Int. Cl.
| | |
|---|---|
| *A61K 31/4172* | (2006.01) |
| *A61K 45/06* | (2006.01) |
| *A61K 31/133* | (2006.01) |
| *A61K 31/198* | (2006.01) |
| *A61K 31/255* | (2006.01) |
| *A61K 31/495* | (2006.01) |

(52) U.S. Cl.
CPC ........ *A61K 31/4172* (2013.01); *A61K 31/133* (2013.01); *A61K 31/198* (2013.01); *A61K 31/255* (2013.01); *A61K 31/495* (2013.01); *A61K 45/06* (2013.01)

(58) Field of Classification Search
None
See application file for complete search history.

(56) References Cited

FOREIGN PATENT DOCUMENTS

WO WO 00/57842 A2 * 10/2000

OTHER PUBLICATIONS

Van Sluis et al. "In Vivo Imgaing of Extracellular pH Using 1H MRSI". Magnetic Resonance in Medicine. 1999; 41:743-750.*
Healing Cancer Naturally [Online]. "Treating Cancer & Destroying Tumors with Baking Soda (Sodium Bicarbonate/Bicarbonate of Soda)". [Retrieved Jun. 13, 2013]. Retrieved from the Internet: <URL: http://www.healingcancernaturally.com/sodium-bicarbonate-treatment.html>. 2007.*
Robey et al. "Bicarbonate Increases Tumor pH and Inhibits Spontaneous Metastases". Cancer Research, Mar. 10, 2009; 69:2260-2268.*
Sigma-Aldrich [Online]. "Sodium Bicarbonate" [Retrieved Jun. 13, 2013]. Retrieved from the Internet: <URL: http://www.sigmaaldrich.com/catalog/product/sigma/s5761?lang=en&region=US>. Two pages.*
Jacob LS. Pharmacology (Fourth Edition). Williams and Wilkins. 1996. pp. 1-13.*
Jacob LS. Pharmacology (Fourth Edition). Williams and Wilkins. 1996. pp. 253-274.*
Raghunand et al. "Enhancement of Chemotherapy by Manipulation of Tumour pH". British Journal of Cancer. 1999; 80(7):1005-1011.*
Robey et al. "Bicarbonate Increases Tumor pH and Inhibits Spontaneous Metastases". Cancer Res. 2009; 69(6):2260-2268.*
Raghunand et al. "Acute Metabolic Alkalosis Enhances Response of C3H Mouse Mammary Tumors to the Weak Base Mitoxantrone". Neoplasia. 2001; 3(3):227-235.*
Silva et al. "The Potential Role of Systemic Buffers in Reducing Intratumoral Extracellular pH and Acid-Mediated Invasion". Cancer Res. 2009; 69(6):2677-2684.*
Hashim et al. "Reduction of Metastasis Using a Non-Volatile Buffer". Clin. Exp. Metastasis. 2011; 28:841-849.*
Martin et al. "Predicting the Safety and Efficacy of Buffer Therapy to Raise Tumour pHe: An Integrative Modelling Study". British Journal of Cancer. 2012; 106:1280-1287.*
Wellcome Trust Sanger Institute [Online]. "The Measure of Man". [Retrieved Feb. 5, 2013]. Retrieved from the Internet<URL: http://www.sanger.ac.uk/about/press/2002/021205.html.> Published Dec. 5, 2002. (Year: 2002).*
N. Raghunand, et al., Acute Metabolic Alkalosis Enhances Response of C3H Mouse Mammary Tumors to the Weak Base Mitoxantrone. Neoplasia, vol. 3, No. 3, 2001, pp. 227-235.
Vannoni, et al., Spontaneous Behavior in the Social Homecage Discrimintes Strains, Lesions and Mutations in Mice. Journal of Neuroscience Methods (2014) pp. 1-12.
Robey, et al., Bicarbonate Increases Tumor pH and Inhibits Spontaneous Metastases. Cancer Res. 2009; 69(6), Mar. 15, 2009; pp. 2260-2268.
Definition of Ad Lib by Merriam-Webster. Date accessed: Jul. 14, 2017: 1 page. https://www.merriam-webster.com/dictionary/ad%20lib#medicalDictionary.

(Continued)

*Primary Examiner* — Leslie A. Royds Draper
(74) *Attorney, Agent, or Firm* — Michele L. Lawson; Smith & Hopen, P.A.

(57) ABSTRACT

A method of treating cancer or inhibiting metastasis in a subject by increasing intratumoral extracellular pH is presented. The method includes administering to the subject a therapeutically effective amount of a buffer having a pKa greater than 6.1. In an advantageous embodiment the pKa of the buffer is about 7.0. Examples of buffers for increasing extracellular pH include $NaHCO_3$, 2-imidazole-1-yl-3-ethoxycarbonylpropionic acid (IEPA), cholamine chloride, N,N-Bis(2-hydroxyethyl)-2-aminoethanesulfonic acid (BES), N-Tris(hydroxymethyl)methyl-2-aminoethanesulfonic acid (TES) and 4-(2-Hydroxyethyl)piperazine-1-ethanesulfonic acid (HEPES). The method can further include the step of pretreating with one or more chemotherapeutic agents.

8 Claims, 13 Drawing Sheets

(56) References Cited

OTHER PUBLICATIONS

Definition of Chronic by Merriam-Webster. Date Accessed: Jul. 14, 2047: 1 page. https://www.merriam-webster.com/dictionary/chronic.
Definition of Repeated by Merriam-Webster. Date Accessed: Jul. 14, 2017: 1 page. https://www.merriam-webster.com/dictionary/repeated.
Freireich et al., Quantitative Comparison of Toxicity of Anticancer Agents in Mouse, Rat, Hamster, Dog, Monkey, and Man. Cancer Chemotherapy Reports. May 1966. vol. 50 (No. 4): 219-244.
Garcia-Martin et al., Mapping Extracellular pH in Rat Brain Gliomas in Vivo by 1H Magnetic Resonance Spectroscopic Imaging: Comparison with Maps of Metabolites. Cancer Research. 2001. vol. 61: 6524-6531.
Raghunand. Tissue pH Measurement by Magnetic Resonance Spectroscopy and Imaging. Methods in Molecular Medicine. 2005. vol. 124: 347-364.

\* cited by examiner

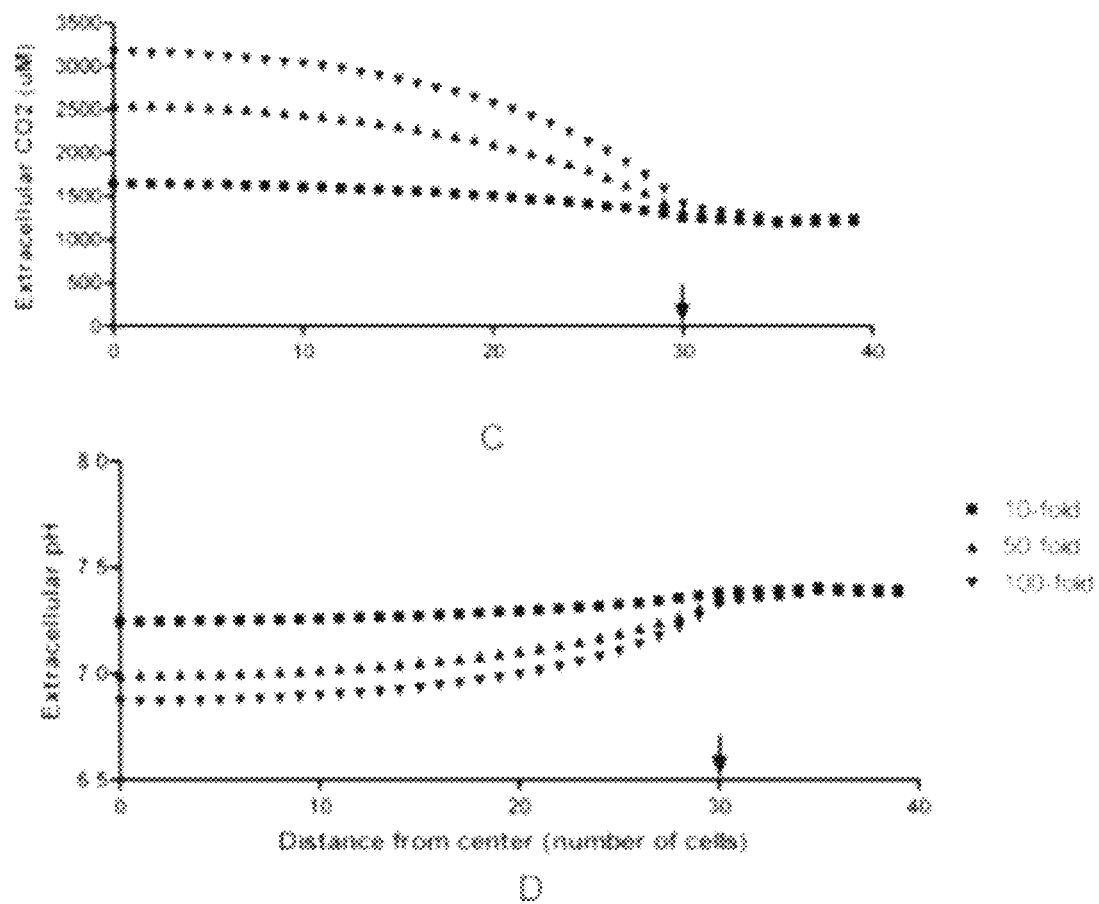
Figure 7 - continued

A.

B.

METHOD OF INCREASING
INTRATUMORAL PHE AND REDUCING
ACID-MEDIATED INVASION

CROSS REFERENCE TO RELATED APPLICATIONS

This application is a continuation of and claims priority to International Application Serial No. PCT/US2010/57991, entitled "Method of Reducing Intratumoral pHe and Acid-Mediated Invasion", filed Nov. 24, 2010 which claims priority to U.S. Provisional Patent Application 61/263,971, entitled, "Method of Reducing Intratumoral pHe and Acid-Mediated Invasion", filed Nov. 24, 2009, the contents of each of which are herein incorporated by reference.

FIELD OF INVENTION

This invention relates to cancer therapy. More specifically, this invention relates to increasing intratumoral extracellular pH and acid-mediated invasion using buffers.

BACKGROUND OF THE INVENTION

A number of studies using pH-sensitive MRI contrast agents, microelectrodes, and MR spectroscopy with hyperpolarized $C^{13}$ have consistently demonstrated that the extracellular pH (pHe) of tumors is significantly lower (6.6-7.0) than healthy tissues (7.2-7.4) [Gillies R J, et al., pH imaging. A review of pH measurement methods and applications in cancers. *IEEE Eng Med Biol Mag* 2004; 23(5):57-64; Gillies R J, et al., MRI of the tumor microenvironment. *J Magn Reson Imaging* 2002; 16(4):430-50; Helmlinger G, et al., Interstitial pH and pO2 gradients in solid tumors in vivo: high-resolution measurements reveal a lack of correlation. *Nat. Med.* 1997; 3(2):177-82; Gallagher F A, et al., Magnetic resonance imaging of pH in vivo using hyperpolarized 13C-labelled bicarbonate. *Nature* 2008; 453(7197):940-3]. This acidity is primarily due to (a) anaerobic glycolysis in tumor regions subjected to short-term or long-term hypoxia as a result of poorly organized vasculature with diminished chaotic blood flow, and (b) aerobic glycolysis (the Warburg effect), a common cancer phenotypic property in which the glycolytic metabolic pathways are used even in the presence of oxygen [Gatenby R A, et al., Why do cancers have high aerobic glycolysis? *Nat Rev Cancer* 2004; 4(11):891-9].

An acidic pHe induces pleiotropic changes in tumor cells. In many tumor types, acute or chronic incubation in a low pH microenvironment increases invasiveness both in vitro and in vivo [Moellering R E, et al., Acid treatment of melanoma cells selects for invasive phenotypes. *Clinical & experimental metastasis* 2008; 25 (4):411-25]. Lowering culture pH to 6.7 has been demonstrated to result in a 4-fold increase in the number of in vivo metastases of the treated cells compared with controls after tail vein injection [Rofstad E K, et al., Acidic extracellular pH promotes experimental metastasis of human melanoma cells in athymic nude mice. *Cancer Res* 2006; 66(13):6699-707; Cuvier C, et al., Exposure to hypoxia, glucose starvation and acidosis: effect on invasive capacity of murine tumor cells and correlation with cathepsin (L+B) secretion. *Clinical & experimental metastasis* 1997; 15(1):19-25; Kalliomaki T, et al., Effects of tumour acidification with glucose+MIBG on the spontaneous metastatic potential of two murine cell lines. *Brit J Cancer* 2004; 90(9):1842-9]. In addition, a variety of cancer cell populations, when exposed to an acidic environment, have been shown to increase expression of interleukin-8 (IL-8), vascular-endothelial growth factor (VEGF), carbon-inc anhydrase IX (CAIX), lactate dehyrodgenase (LDH), cathepsin B, and matrix metalloproteinases (MMP)-2 and MMP-9, all of which are associated with increased tumor growth and invasion in-vivo [Rozhin J, et al., Pericellular pH affects distribution and secretion of cathepsin B in malignant cells. *Cancer Res* 1994; 54(24):6517-25; Xu L, et al., Acidic pH-induced elevation in interleukin 8 expression by human ovarian carcinoma cells. *Cancer Res* 2000; 60(16):4610-6; Shi Q, et al., Regulation of vascular endothelial growth factor expression by acidosis in human cancer cells. *Oncogene* 2001; 20(28):3751-6; Swietach P, et al., Regulation of tumor pH and the role of carbonic anhydrase 9. *Cancer metastasis reviews* 2007; 26(2):299-310]. Interestingly, tumor cells are typically able to maintain high proliferation rates even in an acidic environment [Ceccarini C, et al., pH as a determinant of cellular growth and contact inhibition. *PNAS* 1971; 68(1):229-33].

An acidic pHe, on the other hand, induces significant toxicity in normal cells by reducing proliferation [Id.] and promoting apoptosis via a p53-dependent pathway [Park H J, et al., Acidic environment causes apoptosis by increasing caspase activity. *Brit J Cancer* 1999; 80(12):1892-7] initiated by increasing caspase activity [Williams A C, et al., An acidic environment leads to p53 dependent induction of apoptosis in human adenoma and carcinoma cell lines: implications for clonal selection during colorectal carcinogenesis. *Oncogene* 1999; 18(21):3199-204]. In addition, an acidic pHe in normal tissues increases degradation of the extracellular matrix due to the production and release of proteolytic enzymes [Rozhin J, et al., *Cancer Res* 1994; 54(24):6517-25], promotes angiogenesis through release of VEGF [Shi Q, et al., *Oncogene* 2001; 20(28):3751-6], and limits immune response to tumor antigens [Lardner A. The effects of extracellular pH on immune function. *J Leukocyte Biol* 2001; 69(4):522-30].

These findings have been synthesized into the acid-mediated tumor invasion model, which proposes that intratumoral acidosis results in the flow of $H^+$ ions along concentration gradients into normal tissue adjacent to the tumor. This produces a peritumoral ring of dead and dying cells and a degraded extracellular matrix into which the still viable malignant cells invade [Gatenby R A, et al., A reaction-diffusion model of cancer invasion. *Cancer Res* 1996; 56(24):5745-53; Gatenby R A, et al., Acid-mediated tumor invasion: a multidisciplinary study. *Cancer Res* 2006; 66(10):5216-23]. The model is supported by experimental evidence demonstrating a peritumoral acid gradient associated with normal cell apoptosis and extracellular matrix degradation.

Indirect support for this model is seen in a number of clinical studies, including (a) observations that increased glucose uptake on [18F]fluorodeoxyglucose positron emission tomography scans (and, therefore, increased acid production) in the transition from in situ to invasive cancer [Yasuda S, et al., 18F-FDG PET detection of colonic adenomas. *J Nucl Med* 2001; 42(7):989-92; Abbey C K, et al., In vivo positron-emission tomography imaging of progression and transformation in a mouse model of mammary neoplasia. *PNAS* 2004; 101(31):11438-43] and that a higher level of uptake in many cancer types confers poor prognosis [Schwarzbach M H, et al., Prognostic significance of preoperative [18-F] fluorodeoxyglucose (FDG) positron emission tomography (PET) imaging in patients with resectable soft tissue sarcomas. *Ann Surg* 2005; 241(2):286-94; Schwartz D L, et al., FDG-PET prediction of head and neck squamous cell cancer outcomes. *Arch Otolaryngol* 2004;

130(12):1361-7; Vansteenkiste J, et al., Positron-emission tomography in prognostic and therapeutic assessment of lung cancer: systematic review. *Lancet Oncol* 2004; 5(9): 531-40], (b) increased intratumoral lactate concentrations is associated with a poor prognosis [Walenta S, et al., High lactate levels predict likelihood of metastases, tumor recurrence, and restricted patient survival in human cervical cancers. *Cancer Res* 2000; 60(4):916-21; Schwickert G, et al., Correlation of high lactate levels in human cervical cancer with incidence of metastasis. *Cancer Res* 1995; 55(21):4757-9], and (c) increased expression of proteins that are upregulated by acidic pHe, including IL-8, cathepsin B, lactate dehydrogenase, and carbonic anhydrase IX [Rozhin J, et al., *Cancer Res* 1994; 54(24):6517-25; Xu L, et al., *Cancer Res* 2000; 60(16):4610-6; Shi Q, et al., *Oncogene* 2001; 20(28):3751-6; Swietach P, et al., *Cancer metastasis reviews* 2007; 26(2):299-310; Ceccarini C, et al., *PNAS* 1971; 68(1):229-33] are associated with poor prognosis [Kolev Y, et al., Lactate dehydrogenase-5 (LDH-5) expression in human gastric cancer: association with hypoxia-inducible factor (HIF-1alpha) pathway, angiogenic factors production and poor prognosis. *Ann Surg Oncol* 2008; 15(8):2336-44; Hui E P, et al., Coexpression of hypoxia-inducible factors 1 alpha and 2alpha, carbonic anhydrase IX, and vascular endothelial growth factor in nasopharyngeal carcinoma and relationship to survival. *Clin Cancer Res* 2002; 8(8):2595-604; Choi S W, et al., Expression of carbonic anhydrase IX is associated with postoperative recurrence and poor prognosis in surgically treated oral squamous cell carcinoma. *Hum Pathol* 2008; 39(9):1317-22; Nomura T, et al., Involvement of cathepsins in the invasion, metastasis and proliferation of cancer cells. *J Med Invest* 2005; 52(1-2):1-9; Benoy I H, et al., Increased serum interleukin-8 in patients with early and metastatic breast cancer correlates with early dissemination and survival. *Clin Cancer Res* 2004; 10(20:7157-62].

SUMMARY OF INVENTION

The inventors have discovered that increased systemic concentrations of pH buffers can reduce intra-tumoral and peri-tumoral acidosis and, as a result, inhibit malignant growth. Computer simulations are used to quantify the ability of systemic pH buffers to increase the acidic pHe of tumors in vivo and develop the chemical specifications of an optimal buffer for such purpose. It is demonstrated herein that increased serum concentrations of the sodium bicarbonate ($NaHCO_3$) can be achieved through ingestion. Furthermore, the consequent reduction of tumor acid concentrations is shown to significantly reduce tumor growth and invasion without altering the pH of blood or normal tissues. The simulations also demonstrate the critical parameter governing buffer effectiveness is its pKa. This indicates that $NaHCO_3$, with a pKa of 6.4, is not an ideal intratumoral buffer and that greater intratumoral pHe changes could be obtained using a buffer with a pKa around 7. One such buffer, 2-imidazole-1-yl-3-ethoxycarbonylpropionic acid (IEPA), is demonstrated to be effective in a mouse model. Additional buffers with a pKa around 7 that are candidates include cholamine chloride (pKa 7.1), N,N-Bis(2-hydroxyethyl)-2-aminoethanesulfonic acid ("BES"; pKa 7.15), N-Tris(hydroxymethyl)methyl-2-aminoethanesulfonic acid ("TES"; pKa 7.5), free-base lysine (L-lysine with three pKa's: $pKa_1=2.20$, $pKa_2=8.90$ and $pKa_3=10.28$), or 4-(2-Hydroxyethyl)piperazine-1-ethanesulfonic acid ("HEPES"; pKa 7.55).

Accordingly, in a first aspect the present invention provides a method of treating cancer in a subject by increasing intratumoral extracellular pH. The method includes the step of administering to the subject a therapeutically effective amount of a non-volatile and non-toxic buffer having a pKa greater than about 6.4. In certain embodiments the buffer will have a pKa is between about 6.45 and about 10.3, between about 6.5 and about 8.0, between about 6.8 and about 7.4. In an advantageous embodiment the pKa of the buffer is about 7.0. Examples of buffers for increasing extracellular pH include $NaHCO_3$, 2-imidazole-1-yl-3-ethoxycarbonylpropionic acid (IEPA), cholamine chloride, N,N-Bis(2-hydroxyethyl)-2-aminoethanesulfonic acid (BES), N-Tris(hydroxymethyl)methyl-2-aminoethanesulfonic acid (TES), free-base lysine, and 4-(2-Hydroxyethyl)piperazine-1-ethanesulfonic acid (HEPES).

The method can further include the step of pretreating with at least one chemotherapeutic agent. Advantageously, the buffer is orally administered, though it may be administered by additional routes. Cancers treated by the method include breast cancer, lung cancer, liver cancer, pancreatic cancer, prostate cancer, sarcomas, stomach cancer, testicular cancers, and ovarian cancer.

In a second aspect the present invention provides a method of inhibiting metastasis of cancer cells in a subject by increasing intratumoral extracellular pH. The method includes the step of administering to the subject a therapeutically effective amount of a non-volatile and non-toxic buffer having a pKa between 6.5 and 8.0.

In an advantageous embodiment the pKa of the buffer is about 7.0. Examples of buffers for increasing extracellular pH include $NaHCO_3$, IEPA, cholamine chloride, BES, TES, free-base lysine and HEPES. The method can further include the step of pretreating with at least one chemotherapeutic agent. Advantageously, the buffer is orally administered, though it may be administered by additional routes. Cancer cells treated by the method include breast cancer cells, lung cancer cells, liver cancer cells, pancreatic cancer cells, prostate cancer cells, sarcomas, stomach cancer cells, testicular cancers cells, and ovarian cancer cells.

In a third aspect the present invention provides a kit for treating cancer in a subject comprising a pH buffer and at least one chemotherapeutic agent. In an advantageous embodiment the pKa of the pH buffer is between 6.5 and 8.0. The pH buffer is preferably non-volatile and non-toxic. Examples of buffers to be included in the kit include IEPA, cholamine chloride, BES, TES, free-base lysine, and HEPES.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

A number of studies have demonstrated that the extracellular pH (pHe) in cancers is typically lower than in normal tissue and that an acidic pHe promotes invasive tumor growth in primary and metastatic cancers. The inventors have discovered that increased systemic concentrations of pH buffers can reduce intra-tumoral and peri-tumoral acidosis and, as a result, inhibit malignant growth. Computer simulations are used to quantify the ability of systemic pH buffers to increase the acidic pHe of tumors in vivo and develop the chemical specifications of an optimal buffer for such purpose. It is demonstrated herein that increased serum concentrations of the sodium bicarbonate ($NaHCO_3$) can be achieved through ingestion. Furthermore, the consequent reduction of tumor acid concentrations is shown to significantly reduce tumor growth and invasion without altering the pH of blood or normal tissues. The simulations also demonstrate the critical parameter governing buffer effectiveness is its pKa. This indicates that $NaHCO_3$, with a pKa of 6.4, is not an ideal intratumoral buffer and that greater intratumoral pHe changes could be obtained using a buffer with a pKa around 7. The simulations show that systemic pH buffers can be used to increase the tumor pHe and inhibit tumor invasion.

Figure 1:
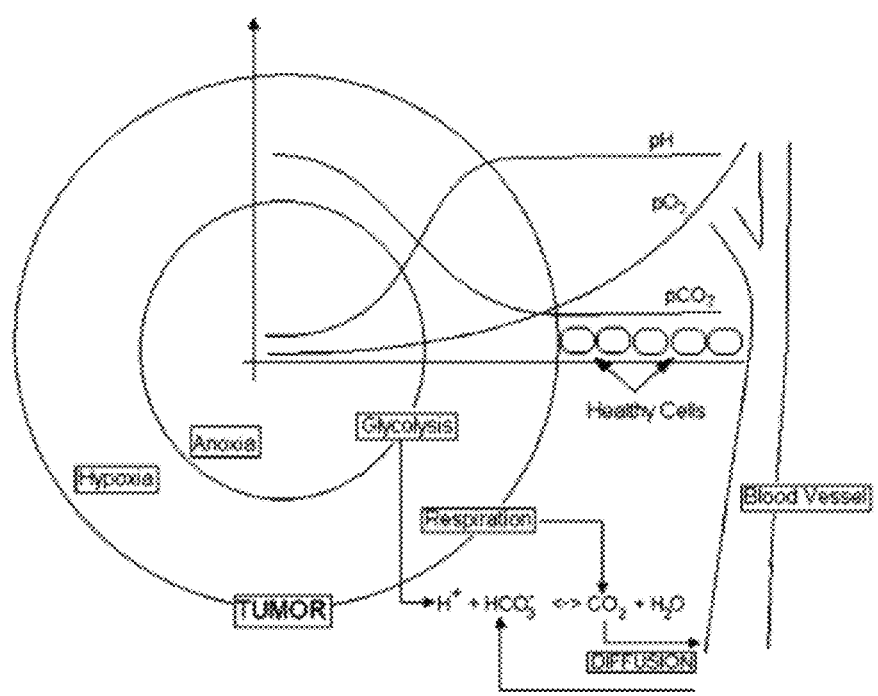
FIG. 1 is an illustration of a tumor microenvironment. An avascular tumor with regions of hypoxia and anoxia produces both carbon dioxide from respiration and protons from anaerobic glycolysis. Bicarbonate buffers the pHe in the tissue by converting protons into water and carbon dioxide. The carbon dioxide then diffuses back to blood vessels and is expelled through the lungs.

If intratumoral acidosis facilitates invasion, then the acid-mediated invasion model can be exploited to devise treatments through the reduction of intra-tumoral and peri-tumoral acid concentrations, thereby inhibiting malignant tumor growth. Sodium bicarbonate ($NaHCO_3$) is one of many physiologic buffers used to control the pH in blood and tissues. Excess $H^+$ combine with bicarbonate and generates water and $CO_2$. Conversely, in environments where $CO_2$ is produced in excess, there is production of bicarbonate and free protons (FIG. 1) from carbon dioxide hydration. Levels of $CO_2$ in tumors have been shown to be higher, and concentrations of bicarbonate lower than in blood or in healthy tissues [Gullino P M, et al., Modifications of the acid-base status of the internal milieu of tumors. *J Natl Cancer* 11965; 34(6):857-69; Helmlinger G, et al., Acid production in glycolysis-impaired tumors provides new insights into tumor metabolism. *Clin Cancer Res* 2002; 8(4): 1284-91].

The effects of increased serum $NaHCO_3$ concentrations on intratumoral pHe, and consequent changes in simulations of tumor growth are demonstrated herein. The chemical specifications of hypothetical buffers are analyzed to determine characteristics of an optimal buffer that may be more efficient than bicarbonate in inhibiting cancer invasion. The critical parameters tested are the dissociation constant (pKa) and the diffusion coefficient.

Figure 2:
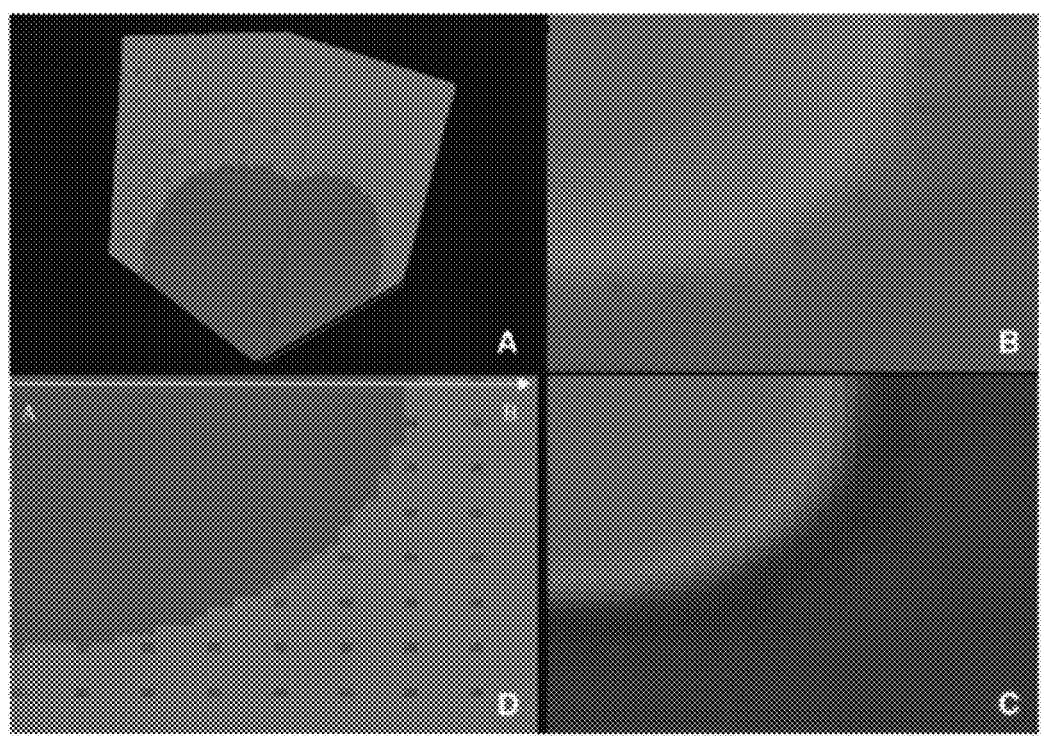
FIG. 2 is a series of images showing TSim's graphical user interface view of the tumor model. The lightly shaded region in the lower portion of the cube in (A) represents one eighth of the tumor sphere. The healthy tissue surrounds the tumor sphere in the cube and is perfused by blood vessels appearing as dots in the cube shown in (A). A planar view of that described for (A) is shown in (D). Simulations allow tumor growth to be simulated along with regional variations in extracellelar pH, as well as $O_2$, $CO_2$, and glucose concentrations as well as intracellular ATP.

Computer and mathematical models have been created to represent the growth and interaction of tumors and healthy tissue [Patel A A, et al., A cellular automaton model of early tumor growth and invasion. *J Theor Biol* 2001; 213(3):315-31; Smallbone K, et al., Metabolic changes during carcinogenesis: potential impact on invasiveness. *J Theor Biol* 2007; 244(4):703-13; Ferreira S C, Jr., et al., Reaction-diffusion model for the growth of avascular tumor. Physical review 2002; 65(2 Pt 0:021907], but none of these models have been used to explore the effects of buffers, such as bicarbonate and phosphates. A 3-D computer model is utilized herein to represent a tumor as a spheroid with a diameter of 60 cells embedded in a healthy, vascularized tissue having a cubic volume 80 cells wide (FIG. 2). This model was analyzed using a tool developed for tissue simulation (TSim from I-Genics) that calculates metabolic reactions, diffusion of species, and buffering effect, as well as cell duplication and apoptosis. The major advantages of using such a representation of the tumor-host environment are that (a) the actual dynamics of the tumor-host interactions are better illustrated by a tridimensional model than by a flattened two-dimensional representation of it, and (b) this representation allows interrogation of the forces that shape the progression or regression of tumors (acidity, energetic metabolism, etc.) without the need of deep mathematical knowledge. This modeling technique is thus able to examine the complex, multiscalar, dynamical, and mutual interactions of molecular, cellular, tissue, and systemic parameters that affect cancer growth and therapy.

Definitions

The term "administration" and variants thereof (e.g., "administering" a compound) in reference to a compound of the invention means introducing the compound into the system of the subject in need of treatment. When a compound of the invention is provided in combination with one or more other active agents (e.g., a cytotoxic agent, etc.), "administration" and its variants are each understood to include concurrent and sequential introduction of the compound and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation or metastasis of the tumor. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, preventing or delaying occurrence or recurrence of cancer, delay or slowing of cancer progression, amelioration of the cancer state, and remission (whether partial or total). The methods of the invention contemplate any one or more of these aspects of treatment.

A "subject in need of treatment" is a mammal with cancer that is life-threatening or that impairs health or shortens the lifespan of the mammal.

A "pharmaceutically acceptable" component is one that is suitable for use with humans and/or animals without undue adverse side effects (such as toxicity, irritation, and allergic response) commensurate with a reasonable benefit/risk ratio.

A "safe and effective amount" refers to the quantity of a component that is sufficient to yield a desired therapeutic response without undue adverse side effects (such as toxicity, irritation, or allergic response) commensurate with a reasonable benefit/risk ratio when used in the manner of this invention.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "comprising" is intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "pretreating", or "pretreatment", is intended to mean that a first treatment is administered prior to, or in conjunction with, a second treatment. In other words, the pretreatment may be performed before another, later treatment, thus allowing the pretreatment time to take effect. Alternatively, the pretreatment may be performed or administered simultaneously with a second treatment without a temporal delay. Advantageously, a pretreatment is administered prior to a second treatment. It is envisioned that pretreatment with a chemotherapeutic agent can be performed 1 hr., 2 hrs., 4 hrs., 8 hrs., 1 day, 2 days, 4 days, 1 week, 2 weeks, or 1 month prior to treatment with a pH buffer, such as a 2-imidazole-1-yl-3-ethoxycarbonylpropionic acid (IEPA). Alternatively, the buffer may be co-administered or administered prior to treatment with additional agents in like intervals.

The present invention also provides a method for treating a patient, comprising administering to said patient simultaneously or sequentially a therapeutically effective amount of a combination of the anti-cancer agent and a pH buffer. In one embodiment the patient is a human that is being treated for cancer. In different embodiments, the anti-cancer agent or treatment and pH buffer are co-administered to the patient in the same formulation; are co-administered to the patient in different formulations; are co-administered to the patient by the same route; or are co-administered to the patient by different routes. In another embodiment one or more other anti-cancer agents can additionally be administered to said patient with the anti-cancer agent/treatment and pH buffer combination. Furthermore, for any of the methods, compositions or kits of the invention described herein where a pH buffer is used, this invention also includes a corresponding method, composition or kit.

Kits for practicing the methods of the invention are further provided. By "kit" is intended any manufacture (e.g., a package or a container) comprising at least one reagent, e.g., a pH buffer of the invention. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

In an advantageous embodiment, the kit containers may further include a pharmaceutically acceptable carrier. The kit may further include a sterile diluent, which is preferably stored in a separate additional container. In another embodiment, the kit further comprises a package insert comprising printed instructions directing the use of a combined treatment of a pH buffer and the anti-cancer agent as a method for treating tumors, tumor metastases, or other cancers in a patient. The kit may also comprise additional containers comprising additional anti-cancer agents, agents that enhance the effect of such agents, or other compounds that improve the efficacy or tolerability of the treatment.

In the context of this invention, other cytotoxic, chemotherapeutic or anti-cancer agents, or compounds that enhance the effects of such agents, include, for example: alkylating agents or agents with an alkylating action, such as cyclophosphamide (CTX; e.g. CYTOXANφ), chlorambucil (CHL; e.g. LEUKERAN®), cisplatin (C is P; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6 MP), 6-thiocguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

As used herein, the term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

In a preferred embodiment, the patient is a human in need of treatment for cancer, or a precancerous condition or lesion, wherein the cancer is preferably breast cancer, lung cancer, liver cancer, ovarian cancer, pancreatic cancer, prostate cancer, sarcomas, stomach cancer, testicular cancers (germ cell), ovarian cancer, transitional cell bladder cancer, bronchogenic lung cancer, thyroid cancer, gastric cancer, lymphomas, mesothelioma, neuroblastoma, soft tissue and osteogenic sarcomas, neuroblastoma, Wilms' tumor, multiple myeloma, malignant lymphoma (Hodgkin's and non-Hodgkin's), acute myeloblastic leukemia, acute lymphoblastic leukemia, Kaposi's sarcoma related to acquired immunodeficiency syndrome (AIDS), bladder cancer, head and neck cancer, thyroid cancer, cancer of the uterus. However, cancers that may be treated by the methods described herein include lung cancer, bronchioloalveolar cell lung cancer, bone cancer, skin cancer, cancer of the head or neck, cutaneous or intraocular melanoma, uterine cancer, ovarian cancer, rectal cancer, cancer of the anal region, stomach cancer, gastric cancer, uterine cancer, carcinoma of the fallopian tubes, carcinoma of the endometrium, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the ureter, carcinoma of the renal pelvis, mesothelioma, hepatocellular cancer, biliary cancer, cancer of the kidney, renal cell carcinoma, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, NSCL, pancreatic, head and neck, colon, prostate, endometrial, renal, bladder, ovarian or breast cancer, or a glioblastoma, fibrosarcoma, or melanoma, including refractory versions of any of the above cancers, or a combination of one or more of the above cancers.

The term "refractory" as used herein is used to define a cancer for which treatment (e.g. chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The anti-cancer agent or treatment will typically be administered to the patient in a dose regimen that provides for the most effective treatment of the cancer (from both efficacy and safety perspectives) for which the patient is being treated, as known in the art. In conducting the treatment method of the present invention, the anti-cancer agent or treatment can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of anti-cancer agent or treatment being used, and the medical judgment of the prescribing physician as based, e.g., on the results of published clinical studies. When the anti-cancer agent or treatment is radiation or a radiochemical, the agent or treatment can be administered in any effective manner known in the art, as described briefly herein, above.

The anti-cancer agent or treatment can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The anti-cancer agent or treatment can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

Methods of preparing pharmaceutical compositions comprising anti-cancer agents or treatments are known in the art. Methods of preparing pharmaceutical compositions are also known in the art. In view of the teaching of the present invention, methods of preparing pharmaceutical compositions comprising both an anti-cancer agent or treatment and pH buffer will be apparent from the art, from other known standard references, such as Remington's Pharmaceutical Sciences, Mack Publishing Company, Easton, Pa., $18^{th}$ edition (1990).

In some embodiments the pKa of the buffer will be greater than 6.1, 6.2, 6.3, 6.4, 6.5, 6.6, 6.7, 6.8, 6.9, 7.0, 7.1 or 7.2 and less than 10.8, 10.6, 10.4, 10.2, 10.0, 9.8, 9.6, 9.4, 9.2, 9.0, 8.8, 8.6, 8.4, 8.2, 8.0, 7.9, 7.8, 7.7, 7.6, 7.5, 7.4, 7.3, 7.2, and combinations thereof. In an advantageous embodiment the pKa will be between 6.5 and 8.0. In further advantageous embodiments the pKa will be between 6.8 and 7.4.

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

The following examples are provided for the purpose of illustration and are not intended to limit the scope of the present invention.

Materials and Methods:

Model: The modeling work focused on small tumors (diameter of about 1.5 mm) to investigate the potential for increased bicarbonate concentrations to delay development of metastases or the transition from microinvasive to clinically apparent primary cancers. Due to the computational effort needed to simulate this model, a fraction of the tumor (one eighth) was chosen for representation considering that the tumor mass is symmetric (FIG. 2).

Most tumors are regarded as spatially heterogeneous, which is a limitation in this model. However, clinical observations have demonstrated that in the tumor size used in these simulations, the assumption of homogeneity in tumoral cell populations is reasonable [Kanamaru H, et al., Analysis of histological heterogeneity in renal cell carcinoma: tumor size-related histological change and its prognostic significance. *Int J Urol* 1996; 3(4):256-60]. The dimensions of the tumor employed in the model is also comparable to small tumors implanted in window chambers in mice [Gatenby R A, et al., Cancer Res 2006; 66(10): 5216-23] and, thus, is valid for comparisons of pHe gradients observed in such experiments.

In this model the cancer cells are more resistant to low pHe than normal cells. In previous works [Patel A A, et al., *J Theor Biol* 2001; 213(3):315-31] the pHe threshold for death of tumor cells was described as being as low as 6.0, but in this a more conservative estimation of 6.4 is employed in the model, while normal cells will not survive in a pHe lower than 6.8.

Tumor cells present increased glucose uptake and metabolism even in the presence of oxygen [Warburg O. On respiratory impairment in cancer cells. *Science* (New York, N.Y. 1956; 124(3215):269-70]. Three cases were considered wherein aerobic glucose metabolism of tumor cells was increased 10-fold, 50-fold and 100-fold compared to normal cells [Patel A A, et al., *J Theor Biol* 2001; 213(3):315-31] and the results are presented in Table 6.

Each cell is considered to be of cubical volume with a side of 25 μm in order to simplify the calculation of the diffusion of species [Smallbone K, et al., *J Theor Biol* 2007; 244(4): 703-13]. The species considered are glucose, $O_2$, $CO_2$, $H^+$, bicarbonate anion, and a hypothetical buffer, where the hypothetical buffer is used to test the tumoral pHe effect of adding a non-$CO_2$-generating buffer with different pKa and diffusion rate. In this model, the concentrations of these species are considered to be constant in the blood vessels.

Figure 3:
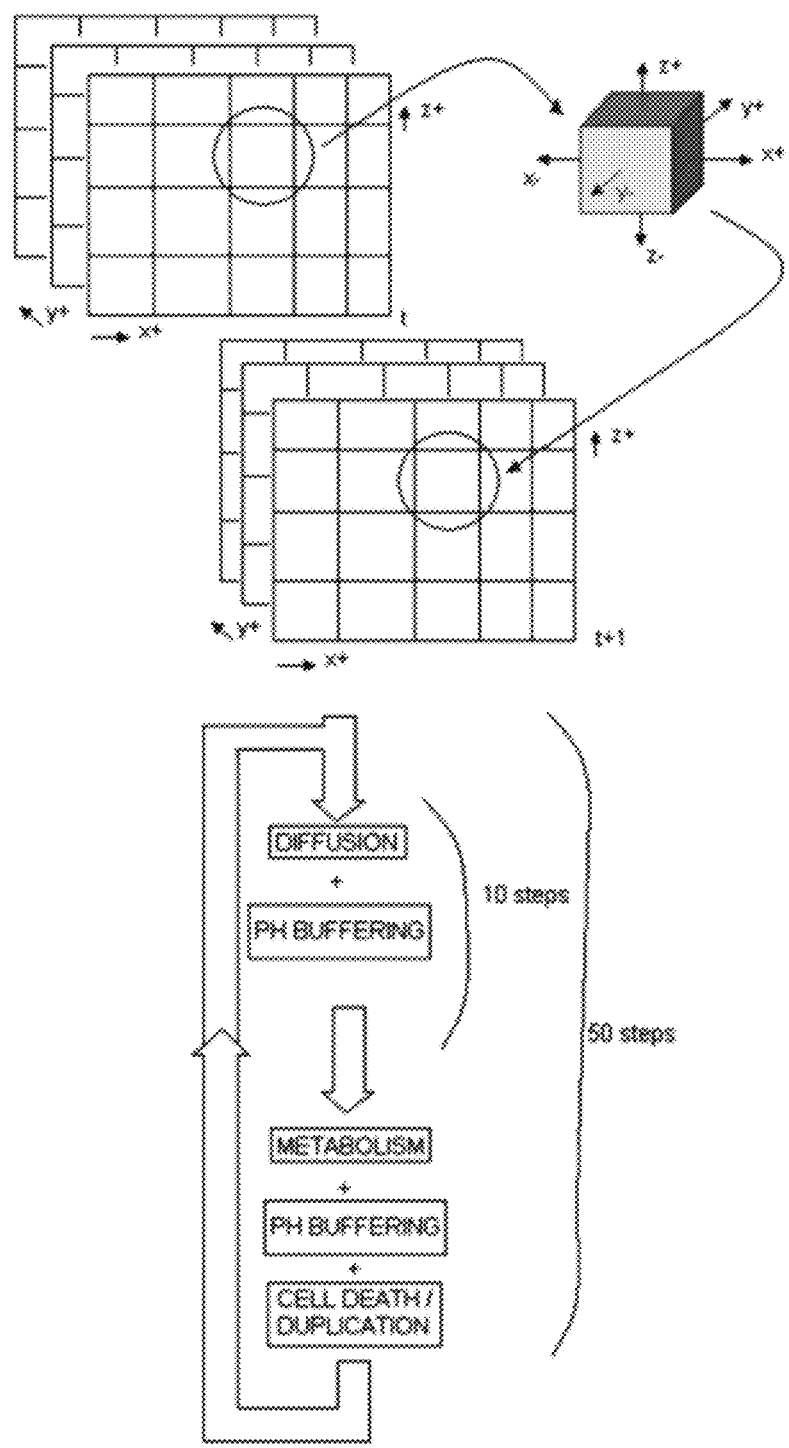
FIG. 3 is an illustration of the simulation. For each volume in simulation space at time t, the diffusion, metabolism, cell duplication and death are calculated and the updated model is stored in the respective volume at time t+1. Diffusion is calculated through an approximation algorithm with steps of one-tenth of a second. Each generation of the simulation is composed of 50 metabolic steps, after which the decision is made on cell fate; (a) duplication, (b) death or (c) remain as is.

Diffusion: The simulation process is composed of two steps: (a) diffusion of the species and (b) cellular activities, including metabolism, proliferation, and death (FIG. 3). The former occurs at a much faster time scale than the latter allowing them to be temporally separated in the simulations.

The diffusion was calculated with an approximation algorithm, which applies the definition of diffusion coefficient to each volume in the simulated space at 0.1 second intervals. The process was repeated ten times to obtain the equilibrium concentrations of species over one second.

$$C_{t+1} = C_t - \left(C_t \times 6 - \sum_{i=1}^{6} C_{it}\right) \times D_N \quad (1)$$

where $C_t$ and $C_{t+1}$ are the concentrations of the species in a volume at times t and t+1 respectively; $C_{it}$ is the concentration of the species in a neighboring volume in time t; and $D_N$ is the diffusion coefficient normalized to the surface between two volumes (25 μm×25 μm) and one-tenth of a second as time frame.

Metabolism, cell duplication and cell death: Once the diffusion steps have been calculated, the software simulates the uptake of glucose and oxygen, glucose metabolism in either aerobic or anaerobic paths and the production of $CO_2$ or lactic acid corresponding to an interval of one second of simulated time.

The uptake of glucose and $O_2$ is proportional to the concentration of these species in the extracellular environment. The transport of $O_2$ into the cell is due to simple Fickian diffusion, whereas the transport of glucose is facilitated by Glut transporters whose genes are often overexpressed in cancer cells [Kunkel M, et al., Overexpression of Glut-1 and increased glucose metabolism in tumors are associated with a poor prognosis in patients with oral squamous cell carcinoma. *Cancer* 2003; 97(4):1015-24; Wykoff C C, et al., Expression of the hypoxia-inducible and tumor-associated carbonic anhydrases in ductal carcinoma in situ of the breast. *Am J Pathol* 2001; 15 8(3): 1011-9].

In this model, the expressions from Smallbone [Smallbone K, et al., *J Theor Biol* 2007; 244(4):703-13] were used for the uptake of $O_2$ and glucose in normal and cancer cells:

$$\text{Uptake}_{O2} = [O_2]_{extracellular} \times K_{O2} \quad (2)$$

$$\text{Uptake}_{Glu\,cos\,e} = [Glu]_{extracellular} \times K_{Glu} \quad (3)$$

$K_{O2}$ is the same for both normal and cancer cells and $K_{Glu}$ varies depending on the type of cancer cell. In this work, the values used for $K_{Glu}$ in tumors were increased 10-fold, 50-fold, and 100-fold as compared to normal cells, reflecting the increase in glucose metabolism.

The energetic metabolism was restricted to glycolysis and TCA cycle. All glucose uptake by the cell was considered to be primarily metabolized into ATP and $CO_2$. The excess of glucose not consumed in respiration is converted into ATP and lactic acid.

$$\text{Glu cos } e + 6 \times O_2 \Rightarrow 36 \times \text{ATP} + 6 \times CO_2 \quad (4)$$

$$\text{Glu cos } e \Rightarrow 2 \times \text{Lactate} + 2 \times H^+ + 2 \times \text{ATP} \quad (5)$$

After 50 metabolic steps (500 diffusion steps) the fate of each cell was decided based on pHe and ATP production:
- If the pHe is lower than the threshold, the cell dies.
- If the ATP production is lower than a threshold for survival (0.85 μM/s), the cell dies [Smallbone K, et al., *J Theor Biol* 2007; 244(4):703-13].
- Should the ATP production rate be above this value, the cell survives with a probability of duplication increasing with ATP production rate, reaching 100% for a value of 8.5 μM/s or higher [Smallbone K, et al., *J Theor Biol* 2007; 244(4):703-13].
- Replication was allowed if there is empty space in the vicinity of the cell (any of the six faces of the cubic volume).

Blood vessels are represented as parallel horizontal lines with a cross-section of one cell of area crossing the simulation space separated by 5 cells, which represents a distance of 125 μm between two blood vessels [Patel A A, et al., A cellular automaton model of early tumor growth and invasion. *J Theor Biol* 2001; 213(3):315-31]. There are no blood vessels in the tumor tissue as this model consists of micrometastasis.

The concentrations of the species in blood and their diffusion coefficients are listed in Tables 1 through 5. The numeric method for calculating the effect of pH buffers is described in Example 1, below.

TABLE 1

Concentration of species in serum and diffusion rates in normal conditions.

| Species | Concentration in Serum (mM) | Diffusion Rate (cm²/s) |
|---|---|---|
| Bicarbonate | 23.8 (Mizumori et al., 2006) | $5 \times 10^{-6}$ (Tanaka et al., 2002) |
| Glucose | 5 | $5 \times 10^{-6}$ (Groebe et al., 1994) |
| Oxygen | 0.15 | $1.5 \times 10^{-5}$ (Nichols & Foster, 1994) |
| $CO_2$ | 1.2 (Mizumori et al., 2006) | $1.5 \times 10^{-5}$ (Tanaka et al., 2002) |
| $H^+$ | $3.98 \times 10-8$ (pH 7.4) | $1.1 \times 10^{-5}$ (Patel et al., 2001) |

TABLE 2

Concentration of species in serum with high bicarbonate concentration (HB).

| Species | Concentration in Serum (mM) |
|---|---|
| Bicarbonate | 33.13 |
| $CO_2$ | 1.66 |

TABLE 3

Concentration of species in serum with very high bicarbonate concentration (VHB).

| Species | Concentration in Serum (mM) |
|---|---|
| Bicarbonate | 47.88 |
| $CO_2$ | 2.4 |

TABLE 4

Concentration of hypothetical buffer in blood serum with pH = 7.4 for assessment of carbon dioxide effect on bicarbonate buffer effect.

| Species | Concentration in Serum (mM) |
|---|---|
| $A^-$ (pKa 6.1) | 9.32 |
| AH (pKa 6.1) | 0.47 |

TABLE 5

Diffusion rates of hypothetical buffer in three different scenarios: slower, faster and same diffusion rate as bicarbonate and $CO_2$.

| Species | Diffusion Rate (cm²/s) |
|---|---|
| $A^-$ (slow) | $2.5 \times 10^{-6}$ |
| AH (slow) | $0.75 \times 10^{-5}$ |
| $A^-$ (normal) | $5 \times 10^{-6}$ |
| AH (normal) | $1.5 \times 10^{-5}$ |
| $A^-$ (fast) | $7.5 \times 10^{-6}$ |
| AH (fast) | $2.25 \times 10^{-5}$ |

Example 1—Computer Model Implementation

Diffusion: The diffusion of species in this model was calculated based on Fick's first law, which relates the diffusion flux through a surface to the difference of concentration of species in volumes separated by this surface (equation 6).

$$J = -D \times \frac{\partial \phi}{\partial x} \quad (6)$$

where J is the diffusion flux expressed as $$\frac{mol}{\mu m^2 \times s},$$

D is the diffusion coefficient in $$\frac{\mu m^2}{s}$$

and $\phi$ is the concentration of a species in $$\frac{mol}{\mu m^3}.$$

Two cubic adjacent volumes in this computer model share a contact surface S=25 µm×25 µm, the distance between centers the two volumes is d=25 µm and the time step used in this calculation is $$\Delta t = \frac{1}{10} s.$$

Under these conditions, the variation in concentration of the two volumes due to diffusion can be approximated as being the product of the flux through the contact surface, during the time step, divided by the volume V:

$$C_{t+1} - C_t = \frac{J \times S \times \Delta t}{V} \quad (7)$$

In the general case, each volume in the model is surrounded by six neighboring volumes, thus the general expression used to calculate the diffusion (equation 1) can be derived from 8:

$$C_{t+1} - C_t = \frac{-D \times \sum_{i=1}^{6}(C_t - C_{it}) \times S \times \Delta t}{d \times V \times 6} = -\sum_{i=1}^{6}(C_t - C_{it}) \times D_N \quad (8)$$

where $D_N$ is a dimensionless constant used to simplify the final expression.

Cell Metabolism: The metabolism of cells in this model, both healthy and cancerous, furthered the work of Smallbone [Smallbone K, et al., *J Theor Biol* 2007; 244(4):703-13]. Considering that a search for a steady-state solution for the system was employed, ignored are the possible transients from the kinetics of the metabolic reactions, and focus was on the stoichiometry of the metabolism of glucose and oxygen into carbon dioxide, lactate, hydrogen ions and ATP.

This simplified mechanism consists of the diffusion of oxygen and glucose from the extracellular environment at fixed rates (simple Fickian diffusion for oxygen and facilitated transport for glucose, equations 2 and 3). Glucose is then metabolized preferentially through respiration (equation 4) and any excess is metabolized anaerobically (equation 5).

This implementation of the model suggests that tumor cells metabolize glucose and produce lactic acid, even in presence of oxygen, not because of malfunctions in mitochondria but due to an excess of glucose metabolism when compared to healthy cells.

Figure 7:
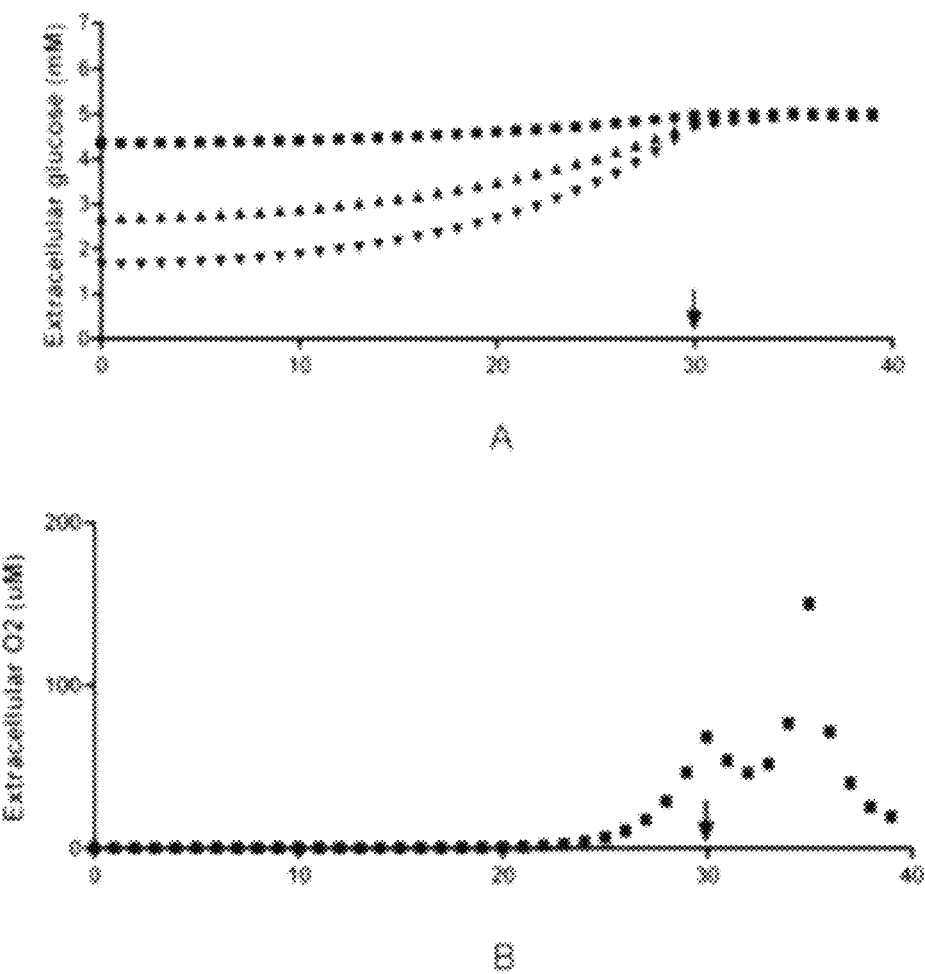
FIG. 7 is a series of graphs illustrating gradients of (A) glucose, (B) $O_2$, (C) $CO_2$ and (D) pHe for three different tumor phenotypes (10-fold, 50-fold and 100-fold increase in glucose metabolism) and normal serum bicarbonate concentration. The vertical arrows mark the tumor-host interface. The spikes of $O_2$ concentration are due to the presence of a blood vessel in position 37 and a second blood vessel at position 31 on an adjacent plane.
Figure 8:
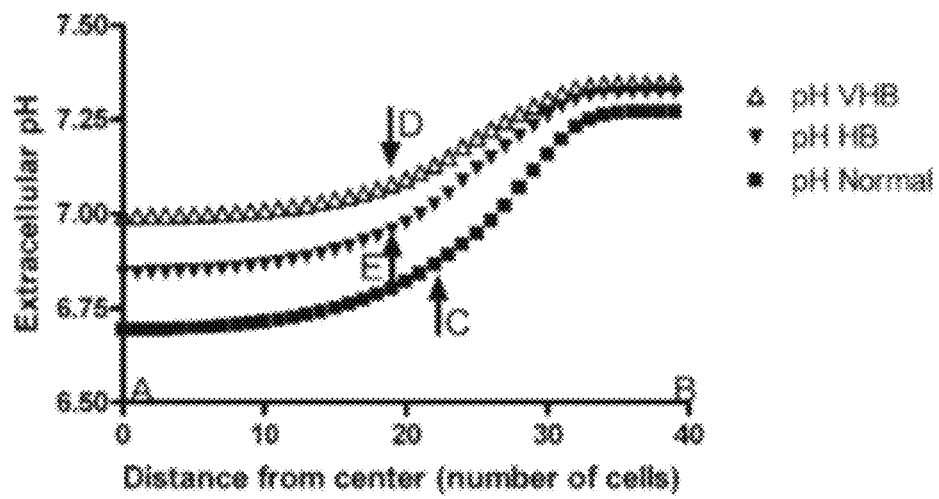
FIG. 8 is a graph illustrating pHe gradients for three tumors of original diameter of 60 cells as described in FIG. 6. After 20 generations the untreated tumor (normal) presents a lower pHe curve and invasion of healthy tissue (C) when compared to tumors treated with bicarbonate (E and D). Concentrations of bicarbonate administered for HB and VHB are as described in the detailed description.

Representative simulations showing distribution of pHe and $CO_2$ in and around tumors are shown in FIG. 7. The effects of increased serum buffers on those distributions are shown in FIG. 8.

Buffer: The combined buffer effect of bicarbonate and the hypothetical buffer was calculated as below. In equilibrium, the concentrations of both buffers are defined by:

$$\frac{[CO_2]}{[HCO_3^-] \times [H^+]} = 10^{pKaBicarb} \quad (9)$$

$$\frac{[AH]}{[A^-] \times [H^+]} = 10^{pKaHypotheticBuffer} \quad (10)$$

When certain amounts of $H^+$ (dH) and $CO_2$ (d$CO_2$) are added to the solution by glycolysis and respiration, there is an unbalance that must be corrected by the transfer (d$X_1$, d$X_2$) of mass from the exceeding species to the rest of the buffer:

$$\frac{(CO_2 + dCO_2 - dX_1)}{(HCO_3^- + dX_1) \times (H^+ + dH + dX_1 + dX_2)} = 10^{pKaBicarb} \quad (11)$$

$$\frac{(AH - dX_2)}{(A^- + dX_2) \times (H^+ + dH + dX_1 + dX_2)} = 10^{pKaHypotheticalBuffer} \quad (12)$$

The solution of this system of equations, where the variables are d$X_1$ and d$X_2$, provides the concentrations of species in the new equilibrium.

Tool Implementation: The model was implemented in the software TSim from i-genics, written in Java. This tool works by simulating the system, one slot at a time (blood vessel, cell or empty space) and stores the resulting simulation space in a file which is next used to compute the following simulation step. The result is a series of snapshots that can be played as a movie or analyzed one frame at a time.

Each simulation was run on a SGI Altix supercomputer and took four hours on four processors to complete with an average requirement 1 GB of memory.

Increases in the precision of the simulation are possible by adding more steps for the diffusion and metabolism. However this slows down the processing time in direct proportion to the number of steps simulated.

Example 2—Validation of Computer Model

Prior to simulation the computer model was validated. Validation was performed by comparing of the curves of pHe, $O_2$, $CO_2$ and glucose concentrations in interstitial fluid both in tumor and healthy tissue with data from previously published experiments.

FIG. 7 depicts profiles of extracellular glucose, extracellular $O_2$, extracellular $CO_2$, and pHe (FIGS. 7A-7D, respectively) in the tumor and healthy tissue. All charts correspond to measurements along the top horizontal line spanning from the center of the tumor adjacent to the healthy tissue (FIG. 2—horizontal line from A to B in FIG. 2D).

Glucose: The simulations showed a slight decrease on the concentration of glucose in the healthy tissue (FIG. 7A) because the cells are further away from blood vessels. There was a steeper decrease in the availability of glucose further into the tumor tissue due to both the increased uptake of glucose and the lack of vascularization, consistent with other models [Smallbone K, et al., *J Theor Biol* 2007; 244(4): 703-13].

pO2: The results from the simulations are consistent with previous measurements [Helmlinger G, et al., *Nat. Med.* 1997; 3(2):177-82] that showed a decrease in $pO_2$ from serum levels to practically zero in a distance of 200 µm (corresponding to 8 cells in this computer model). In the model this profile remained unchanged, irrespective to the addition of buffers (data not shown) or the glycolytic phenotype of the cancer cells simulated (FIG. 7B).

pCO2: The $CO_2$ concentration curve (FIG. 7C) showed increased levels of carbon dioxide in cells located further from blood vessels. The levels of $CO_2$ in tumors were between 25% and 125% higher than in blood serum, which is in accordance with values previously measured in vivo [Gullino P M, et al., *J Natl Cancer I* 1965; 34(6):857-69; Helmlinger G, et al., Acid production in glycolysis-impaired tumors provides new insights into tumor metabolism. *Clin Cancer Res* 2002; 8(4):1284-91].

pHe: The extracellular pH (pHe) of the tumors in the model decreased as a function of the distance from the blood vessels, and also with the increased metabolism of glucose into lactic acid (FIG. 7D). In the three tumor phenotypes considered there was no presence of necrotic core.

The pHe curves obtained were consistent with the range of values found in previous in vivo experiments [Helmlinger G, et al., *Nat. Med.* 1997; 3(2):177-82; Gatenby R A, et al., *Cancer Res* 2006; 66(10):5216-23; Martin G R, et al., Noninvasive measurement of interstitial pH profiles in normal and neoplastic tissue using fluorescence ratio imaging microscopy. *Cancer Res* 1994; 54(20:5670-4].

Example 3—Simulation Results

The effect of the addition of buffers to the blood serum in the pH of tumors was evaluated. This was tested first using bicarbonate, which is readily available, and then comparing these results to hypothetical buffers of different pKa values and diffusion coefficients.

Variation of bicarbonate concentration: The first test performed was an increase in the bicarbonate buffer concentration in blood serum, simulating the chronic ingestion of bicarbonate in order to evaluate the effect of increased doses of this buffer in the pHe in the tumor-host interface.

Figure 4:
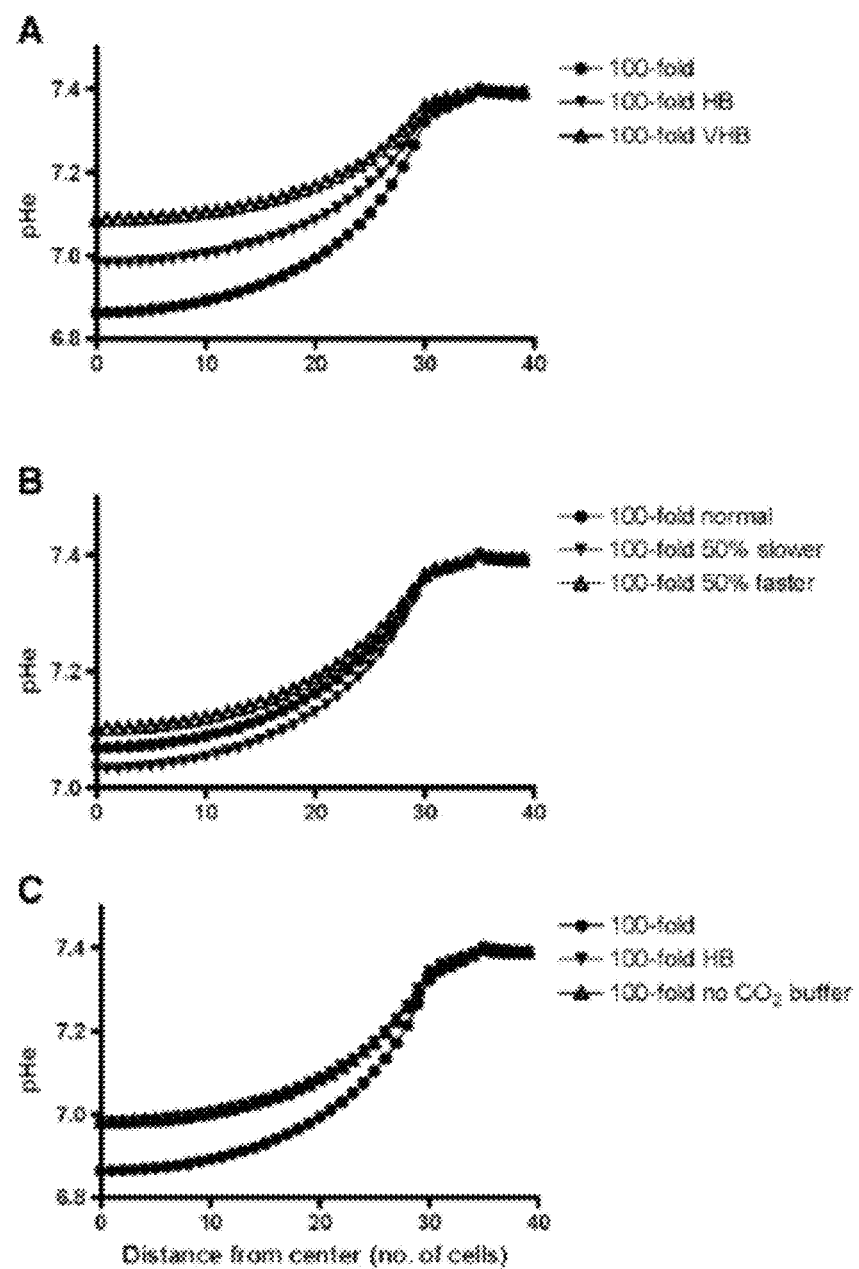
FIG. 4 is a series of graphs illustrating the dependency of the pHe gradient on the diffusion rate under a variety of conditions. In (A) the effects of increased serum bicarbonate concentration on pHe gradient in tumors with 100-fold increase in glucose metabolism. The graph in (B) shows the dependency of pHe gradient on the diffusion rate of a hypothetical buffer added to serum. In (C) the pHe gradient produced by a hypothetical non-$CO_2$ producing buffer as compared to bicarbonate confirms that no noticeable difference exists if the other chemical properties (i.e. pK) are kept equal for the two buffers.

FIG. 4A shows curves representing the pHe gradient for the scenario of 100-fold increase in tumor glucose metabolism and three bicarbonate buffer concentrations as shown in Tables 1, 2 and 3, representing a total of 25, 35 and 50 mM of total buffer in blood serum respectively ($HCO_3^-$+$CO_2$), identified as normal, high bicarbonate (HB) and very high bicarbonate (VHB) concentrations. This is based on a range of serum concentrations that are achievable with ingestion of $NaHCO_3$ in amounts up to 70 grams per day.

The results showed that for the less glycolytic tumor (10-fold increase), the highest bicarbonate concentration increased the pHe in the center of the tumor from 7.25 to 7.32 while the pHe in the rim rose from 7.38 to 7.39 (data not shown). In the most glycolytic tumors (100-fold increase), the same amount of bicarbonate resulted in an increase of pHe from 6.86 to 7.09 in the center and 7.32 to 7.36 in the tumor rim.

In the computer model, the increases in total serum buffer concentration were 40% (HB) and 100% (VHB). The pHe profile for 40% increase (FIG. 4A) demonstrates that the flattening of the pHe curve in tumors can be explained by the effect of bicarbonate.

Diffusion rate of hypothetical buffer: The effect of the diffusion rate of a hypothetical buffer used in conjunction with physiologic bicarbonate was investigated. A buffer that diffuses faster should more efficiently remove the excess of protons generated by the anaerobic glycolytic metabolism.

As before, simulations were performed considering three different scenarios for the glucose metabolism of tumor cells. In all cases (FIG. 4B) simulations were performed under high serum levels of bicarbonate plus a hypothetical buffer with arbitrary pKa 8 and three different diffusion rates: (a) a diffusion rate equal to that of bicarbonate and $CO_2$; (b) a 50% lower diffusion rate; and (c) a 50% higher diffusion rate. Diffusion coefficients of these hypothetical buffers are shown in Table 5.

As expected, the buffer with a faster diffusion rate had the most noticeable effect on increasing the pHe. The differences between the slowest and the fastest buffers were 0.02, 0.05 and 0.08 pH units in the tumor center for 10-fold, 50-fold (data not shown) and 100-fold glycolysis increases, respectively.

The effect of buffers with different diffusion rates is less noticeable than that observed for buffers with different pKa values. Therefore, the diffusion rate while contributing to changes in pHe, does not seem not to be the most critical parameter to consider in the choice of an alternative buffer.

Bicarbonate combined with non-$CO_2$-generating buffer: Tumors are subject to heterogeneous external conditions. For example, the rim might be exposed to normoxia while the core is hypoxic. While lactic acid is produced by anaerobic metabolism in the tumor center, a reasonable amount of $CO_2$ might be generated by respiration in the tumor rim. Due to lack of vascularization in the center of the tumor, carbon dioxide could accumulate inside the tumor, increasing acidity and reducing the efficiency of the bicarbonate buffer.

The results of two scenarios were compared. In the first case, a certain amount of bicarbonate was added to blood (10 mM). In the second case, the same amount was added in the form of a hypothetical buffer with pKa 6.1 and diffusion coefficients equal to the ones of bicarbonate buffer ($A^-$ equal to $HCO_3^-$ and AH equal to $CO_2$ diffusion respectively). In both cases the total buffer concentration in blood was the same (35 mmol/L). The concentrations for this buffer in blood serum are shown in Table 4.

The simulations show that the pHe curve was not affected by the use of a non-$CO_2$ generating buffer (FIG. 4C). Considering that the diffusion rate of $CO_2$ is three times faster than bicarbonate (Table 1), the limiting factor for the removal of free protons from the tumor is bicarbonate and not carbon dioxide.

Figure 6:
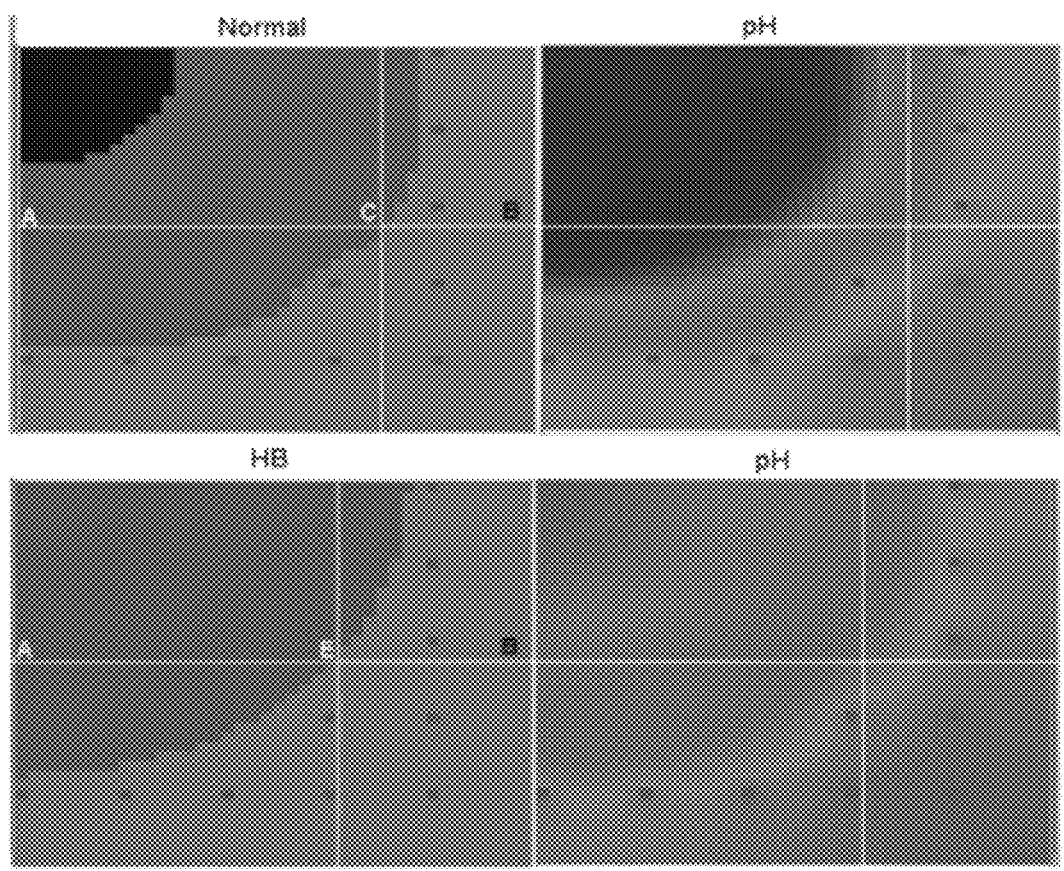
FIG. 6 illustrates pHe distributions in and around tumors along with tumor growth after 20 generations with normal (top row) serum bicarbonate and with a 40% increase in concentration. As outlined in the text, the pHe was much less acidic in the presence of the increased serum buffer, resulting in a dramatic reduction in tumor invasion.

Bicarbonate combined with buffers with different pKa: Buffers with the same concentration in blood serum (~18 mM) were tested with different pKa values ranging from 6.2 to 8.0, at intervals of 0.2 pH units (FIG. 6).

In all simulated tumors, the more noticeable effect was the buffer with pKa equal to 7. This can be explained by the better efficiency of a pH buffer when it is used in a solution with pH in the range of one pH unit above or below the buffer pKa.

The pH maintained in blood in this model is 7.4, and the pH in the center of the tumor is close to 6.8. Thus, a buffer with a pKa close to the average of these values (~7) should prove more effective in absorbing the protons produced by the tumor.

Heterogeneity of tumor energetic metabolism: Tumors with increased glycolytic consumption, on the order of magnitude of 50-fold or 100-fold, presented an ATP production profile that reflected the decrease of the concentration of glucose on the environment. For these tumors, most of the energy was obtained from anaerobic glycolysis (>97% for 50-fold and >97.5% for 100-fold), even in the rim (data not shown).

Tumors with lower glucose uptake presented a combination of two behaviors: On the rim of the tumor (around three cells deep), the energy was obtained mostly by aerobic glucose metabolism (~92%), but at concentrations of oxygen below ~18 µM, the metabolism switched to anaerobic glycolysis, with >96% of ATP produced anaerobically at a distance five cells away from tumor-healthy tissue interface (data not shown).

Tumor growth with increased concentrations of bicarbonate: To estimate the effect of increasing pH buffer availability and consequent reduction of the pHe gradient in tumor invasion, three scenarios were tested: normal bicarbonate concentration, HB concentration, and VHB concentration. The HB group corresponded to the bicarbonate concentration expected with ingestion of 40 g of $NaHCO_3$ per day by a 70 kg man (see case report in discussion, below). The HB group represented 40% of the VHB dose. Each scenario was run for 20 generations. At the end of each generation, the cells being allowed to duplicate, die or remain unchanged.

The tumor growth and pHe gradients for normal and HB concentrations are depicted in FIGS. 6 and 8. With normal serum concentrations of bicarbonate, the tumor cells were highly acidotic, creating a significant peritumoral pHe gradient that extensively invaded into the normal tissue. Addition of a moderate amount of bicarbonate in blood (approximately 40% increase in serum concentration) reduced the amount of intra-tumoral and peri-tumoral acidosis and almost completely eliminated tumor invasion (loss of only 12 healthy cells out of more than 48,000). Treatment with higher bicarbonate (Table 7) concentrations totally prevented invasion (no loss of normal cells). Note that both treatment scenarios also eliminated the necrotic tumor core that developed with normal bicarbonate concentrations—a potential imaging tumor biomarker for clinical trials.

TABLE 6

Uptake constants for $O_2$ and glucose.

| Constant | Uptake ($s^{-1}$) |
| --- | --- |
| $K_{O2}$ | $9.41 \times 10^{-2}$ (Smallbone et al., 2006) |
| $K_{Glu}$ (normal cell) | $1 \times 10^{-5}$ (Patel et al., 2001) |
| $K_{Glu}$ (cancer 10x) | $1 \times 10^{-4}$ |
| $K_{Glu}$ (cancer 50x) | $5 \times 10^{-4}$ |
| $K_{Glu}$ (cancer 100x) | $1 \times 10^{-3}$ |

TABLE 7

Number of healthy and tumor cells for each scenario tested.

| Scenario | Number of Healthy Cells | Number of Tumoral Cells | Volume of Tumor (mm$^3$) |
| --- | --- | --- | --- |
| Very High Bicarbonate (VHB) | 48,113 | 15,216 | $2.38 \times 10^{-1}$ |
| High Bicarbonate (HB) | 48,101 | 15,228 | $2.38 \times 10^{-1}$ |
| Normal | 45,786 | 16,332 | $3.63 \times 10^{-1}$ |
| Original State | 48,113 | 15,216 | $2.38 \times 10^{-1}$ |

*Despite the loss of tumor cells due to the necrotic core, the scenario with less bicarbonate presents more tumor cells due to the invasion of healthy tissue.

Example 4—In Vivo Use of IEPA as a Non-Volatile Buffer

The tumor microenvironment is acidic as a consequence of upregulated glycolysis and poor perfusion. The inventors have previously demonstrated [Robey I F, et al., Bicarbonate Increases Tumor pH and Inhibits Spontaneous Metastases in Mice. Cancer Res. 2009; 69(6):2260-68] that spontaneous and experimental metastases can be inhibited by chronic consumption of sodium bicarbonate solution. Here, with reference to FIGS. 10-13, it is demonstrated that the anti-metastatic effect is not specific for bicarbonate, but can also be seen with non-volatile buffers. In these experiments, 10 mice were provided with ad libidum 200 mM of 2-imidazole-1-yl-3-ethoxycarbonylpropionic acid (IEPA) in their drinking water and 10 mice were maintained on water.

Four days after initiation of therapy, all animals were injected with luciferase-expressing PC3M prostate cancer cells. Animals were imaged weekly to follow metastasis, and, similar to bicarbonate, animals treated with buffered water had significantly fewer lung metastases compared to the control group (p<0.02). As with bicarbonate, weight gain and grooming behavior in IEPA treated mice were not different from controls. This result is consistent with the mathematical model presented above [see also: Silva A S, et al., The potential role of systemic buffers in reducing intra-tumoral extracellular pH and acid-mediated invasion. Cancer research 2009; 69(6):2677-84] that predicted that buffers with $pK_a$ of ~7 would yield anti-metastatic results similar to or better than those obtained with bicarbonate (pKa 6.1). IEPA buffer was chosen over other systemic pH buffers (TRIS, HEPES) because the inventors have used it in vivo in the past and it has been shown to be non-toxic at high doses [Bhujwalla Z M, et al., Combined vascular and extracellular pH imaging of solid tumors. NMR in biomedicine 2002; 15(2):114-9; van Sluis R, et al., In vivo imaging of extracellular pH using 1H MRSI. Magn Reson Med 1999; 41(4):743-50]. Therefore, all non-toxic, non-volatile buffers are contemplated by the invention. Moreover, the invention is not limited to cancers/tumors discussed herein and extends to other cancers, as bicarbonate therapy has been effective in breast and lung cancers as well.

Discussion: Three-dimensional mathematical models were used to quantify the ability of systemic buffers to reduce the acidity of tumors and peritumoral normal tissue. The acid-mediated tumor invasion model suggests that reduction of the intra-tumoral and peri-tumoral pHe gradients will also reduce tumor growth and invasion. It has been demonstrated herein that clinically achievable concentrations of NaHCO$_3$ can reduce malignant tumor growth and, thus, have value as a clinical therapy.

The simulations demonstrate that increased concentration of serum bicarbonate can decrease intra-tumoral and peritumoral acidosis without altering blood pH. This might, at first, appear paradoxical. However, the treatment is not "alkalization", but rather, treatment with a physiological buffer. The effect of the former is to produce a generalized increase in pH. By contrast, the effect of increasing the concentration of a physiologic buffer is to drive the entire system toward a normal pH (i.e. 7.35-7.45). Thus, regions that are at normal pH (such as blood) will not be affected while regions at abnormal pH (either acidic or alkaline) will tend toward physiologic values.

A number of observations from the computer simulations can be made. First, there is a linear relationship between the amount of bicarbonate in blood and the pHe in tumors of the size simulated in this work, even though the pH in blood remains unchanged. Second, the use of a non-CO$_2$-generating buffer with same pKa and diffusion rates as bicarbonate does not provide advantages over bicarbonate, indicating that the byproduct carbon dioxide is not the limiting factor in the efficiency of bicarbonate buffer. Third, the pKa of a hypothetical buffer is the most important characteristic on its effect on the tumor pHe. The proposed pKa in this study is around seven ("7"). Fourth, the diffusion coefficient of a hypothetical buffer generates less noticeable effects if compared to different pKa, and thus is not the main parameter to be considered in the choice of an alternative buffer. Lastly, moderate increases in the serum NaHCO$_3$ concentrations will substantially reduce intra-tumoral and peri-tumoral acidity, which will virtually eliminate tumor invasion into normal adjacent tissue resulting in stable tumor size.

The results presented herein with respect to NaHCO$_3$ are consistent with data measured in window chambers in a companion project [Robey I F, et al., Bicarbonate Increases Tumor pH and Inhibits Spontaneous Metastases in Mice. Cancer Res. 2009; 69(6):2260-68] and in previous work [Gullino P M, et al., Modifications of the acid-base status of the internal milieu of tumors. J Natl Cancer 11965; 34(6): 857-69]. The size of the tumor in the simulations is comparable to those measured in the experimental window chamber model (1.5 mm diameter for the simulated tumor and 1.4 mm for the window chamber) and, the pHe gradients from FIG. 4 fit quantitatively the experimental curves (6.86 in center and 7.09 in rim for the simulated tumors (FIG. 4) and 6.9 in center and 7.15 in rim measured experimentally [Gatenby R A, et al., Cancer Res 2006; 66(10):5216-23; Robey I F, et al., Cancer Res. 2009; 69(6):2260-68].

Figure 5:
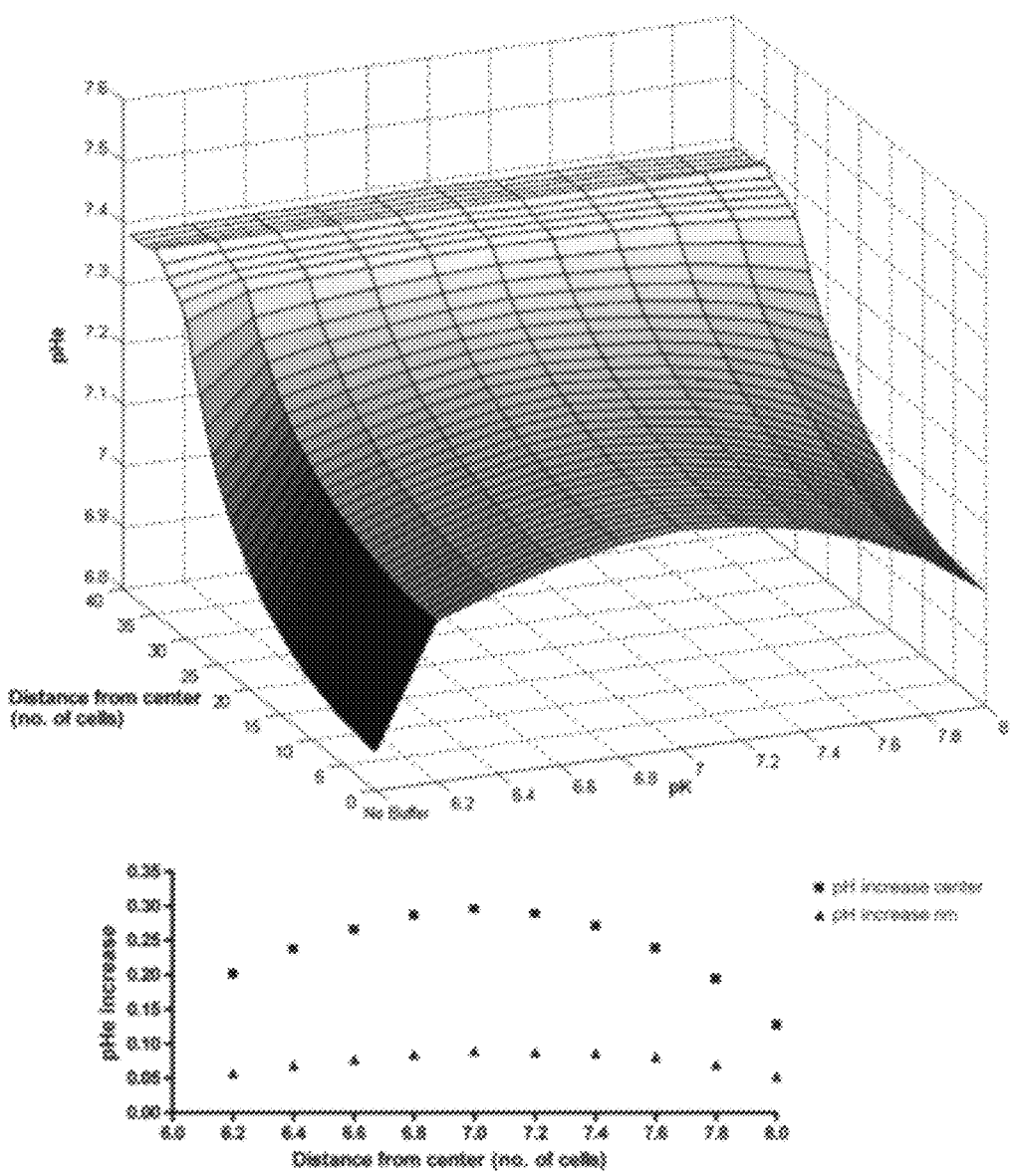
FIG. 5 shows the dependency of pHe gradient on the value of hypothetical buffer's pKa and comparison with no treatment. In the inset, the pHe raise (in pH units) in tumor center and tumor rim.

The pHe curves in and around tumors obtained in the simulations with normal and elevated serum concentrations of NaHCO$_3$ can be compared to experimentally-determined acid concentrations [Robey I F, et al., Cancer Res. 2009; 69(6):2260-68]. In the Robey et al. study, GFP-labelled MDA-mb-231 tumors were grown in window chambers in SCID mice. Bicarbonate concentrations were increased by adding 200 mM of NaHCO$_3$ to the drinking water. This was calculated to be the equivalent of a daily dose of 37 g in a 70 kg human. The pHe gradient in the tumor and pertitumoral normal tissues was measured using fluorescent ratio imaging. As shown in FIG. 5 of Robey et al., the pHe gradients of the tumor increased 0.1 to 0.2 pH units when the bicarbonate was added to the water, which is very similar to the changes observed in the computer simulations presented herein.

The clinical feasibility of chronic ingestion of bicarbonate to reduce tumor invasion is a consideration. Interestingly, NaHCO$_3$ is readily available in grocery stores (as baking soda) and in over-the-counter preparations for clinical use as an antacid. The recommended daily dose is 5 teaspoons a day, which is 25-50 grams, where the variation depends on the degree of "heaping" in the teaspoon. Such a dosage has been administered chronically (i.e. greater than 1 year) in patients with renal tubular acidosis (RTA) and sickle cell anemia without adverse affects [Booth B E, et al., Grocery store baking soda. A source of sodium bicarbonate in the management of chronic metabolic acidosis. *Clin Pediatr* 1984; 23(2):94-6; Mann J R, et al., Sodium bicarbonate prophylaxis of sickle cell crisis. *Pediatrics* 1974; 53(3):414-6].

Finally, the experience of a 79 year-old man with widely metastatic renal cancer followed at the Moffitt Cancer Center is included as further evidence of efficacy. The subject presented with hematuria in January 2004 and was found to have a large right renal cancer with clot extending into the inferior vena cava (stage T3b, N2, Mx). He underwent a nephrectomy with clot removal at the Moffitt Cancer Center in February, 2004. In June, 2005, he developed metastatic disease in his liver. He was treated with Sutent, but the tumor progressed with metastases developing in the subcutaneous tissues and retroperitoneal lymph nodes. He was unable to tolerate ALT-801.

Figure 9:
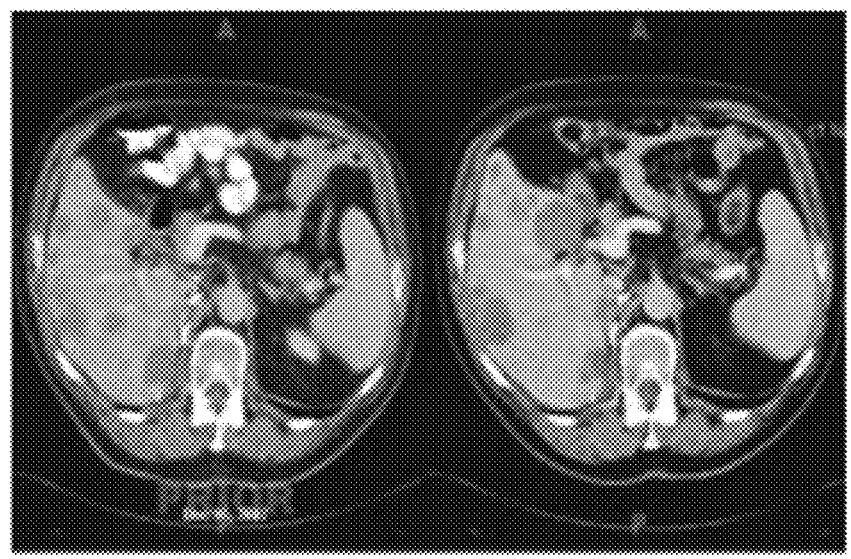
FIG. 9 is an image showing CT scans of the liver from a patient with metastatic renal cancer who self-administered 40 grams of $NaHCO_3$ daily and received no conventional therapy after Sep. 1, 2007. Scans from Dec. 5, 2007 (left) and Apr. 18, 2008 (right) are shown. The images are representative in that some of the liver lesions have increased in size, some have decreased in size, and some have remained stable. Notably, the central necrosis seen in several of the tumors on the initial scan was no longer present in the follow-up scan.
Figure 10:
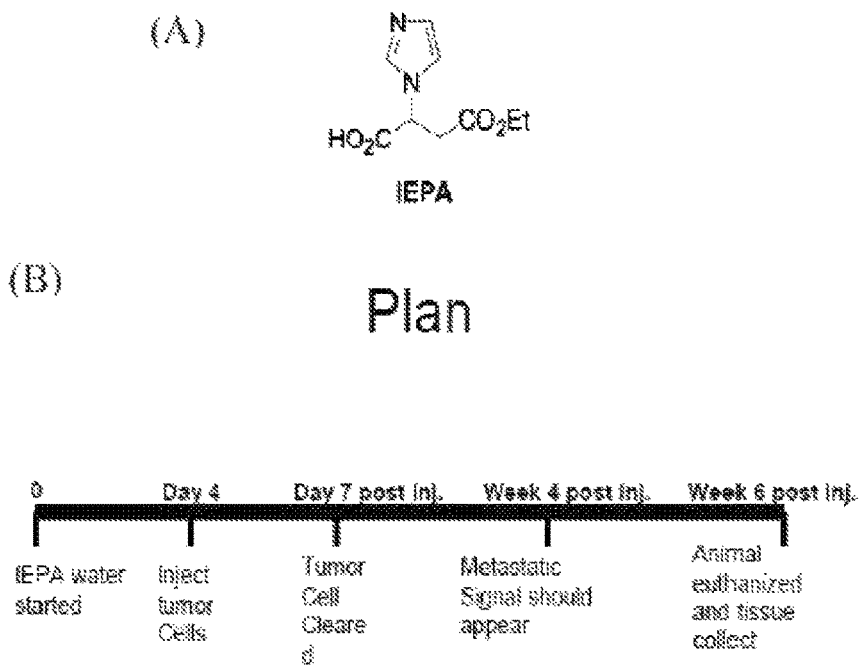
FIG. 10 illustrates (A) the chemical structure of IEPA and (B) an experimental timetable. For the experiment mice (n=10) were started on 200 mM IEPA, or tap water (n=10) at time 0. Four days later 5×10⁶ PC3M cells were injected intravenously in to the mice. Images were acquired weekly, and animal were euthanized at week 6 post-injections.
Figure 11:
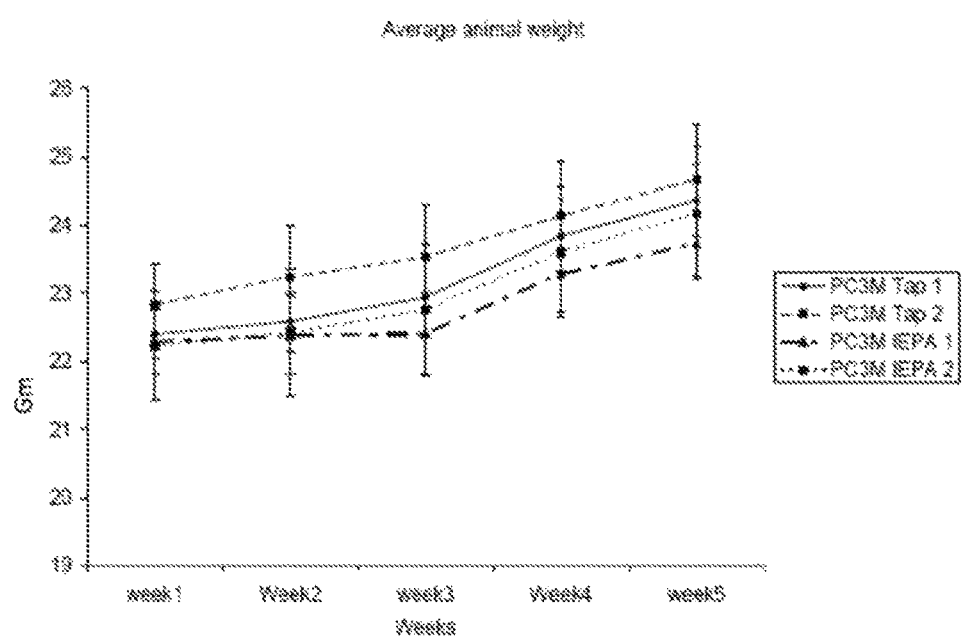
FIG. 11 is a graph illustrating the animal weight average from the experiment as discussed in FIG. 10. Animals were weighed daily through the course of the experiment, and a weekly average is shown in the graph. No significant difference in animal weight among all groups was observed.
Figure 12A:
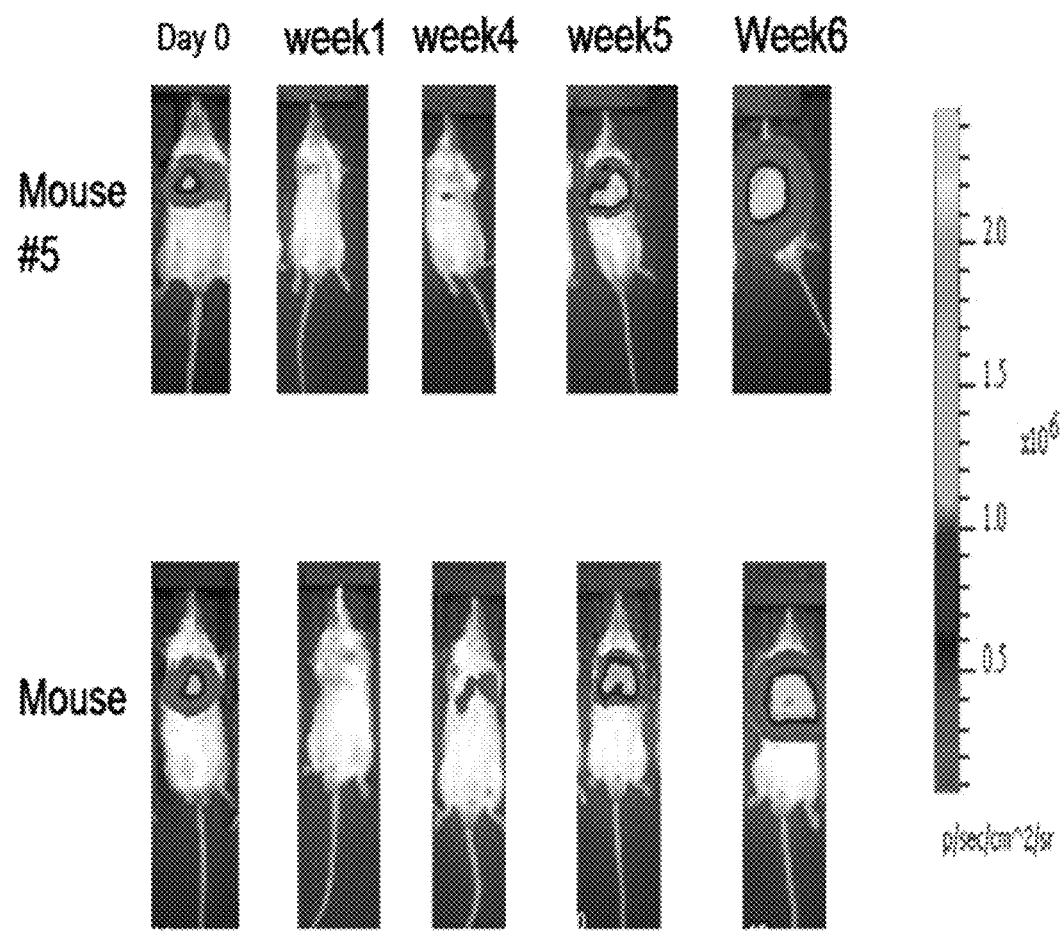
FIG. 12 is a series of images illustrating that IEPA significantly inhibits lung metastasis. Mice were imaged in a ventral view weekly for 6 weeks using the in vivo Imaging System (IVIS, Xenogen). (A) Control mice developed lung metastasis by week 4, as illustrated by mouse #5 and mouse #8. (B) IEPA treated mice showing little to no tumor metastasis as illustrated by mouse #12 and mouse 18.
Figure 12B:
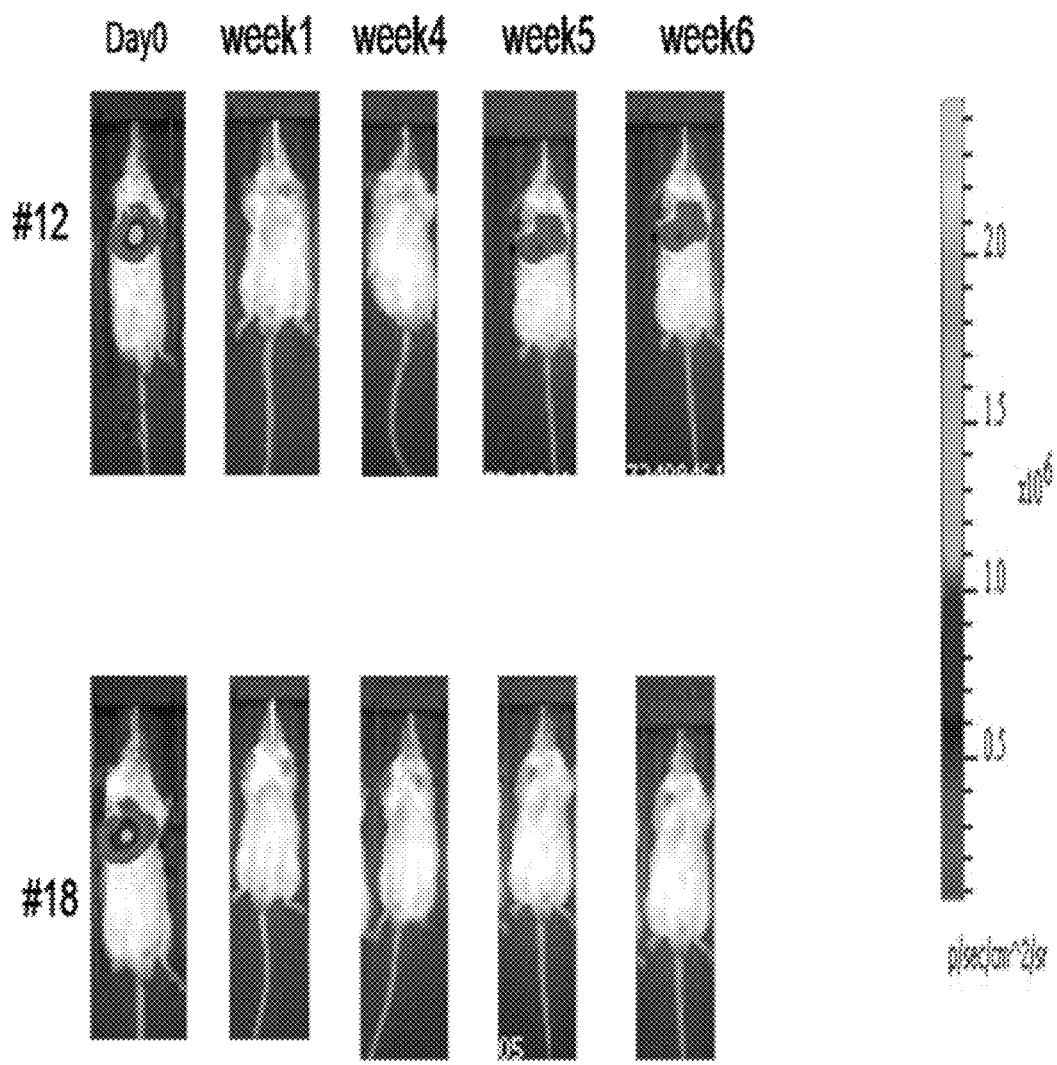
Figure 13:
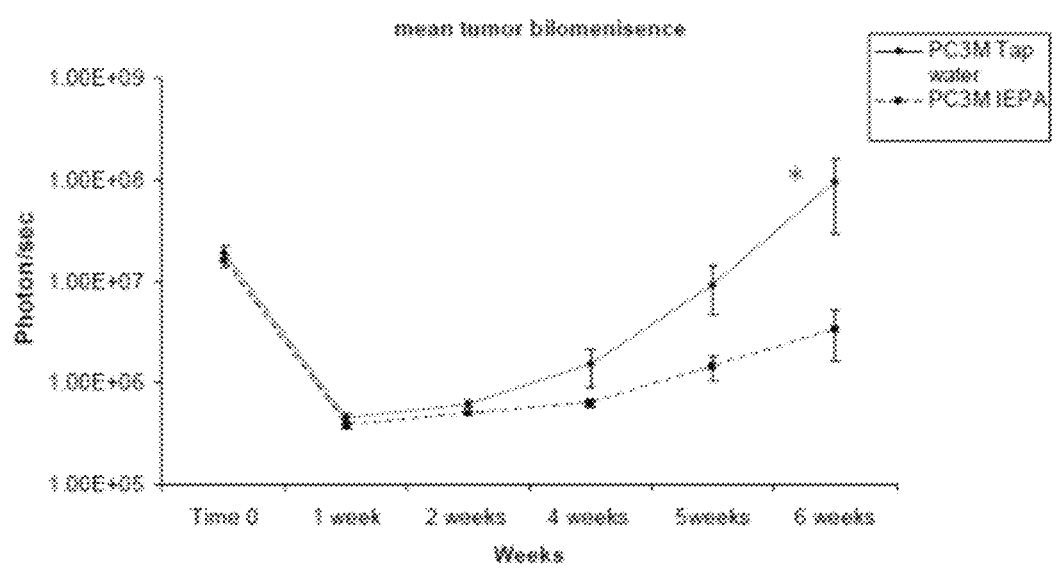
FIG. 13 is a pair of graphs illustrating the mean in vivo photon count for the whole animal (A), and lungs (B). A region of interest (ROI) was manually selected over the signal intensity. The area of the ROI was kept constant and the intensity was recorded as maximum [photons/sec]. The IEPA-treated group was significantly different (*$p<0.002$ using Wilcoxon—two sample test) than the tap water group.
Figure 13:
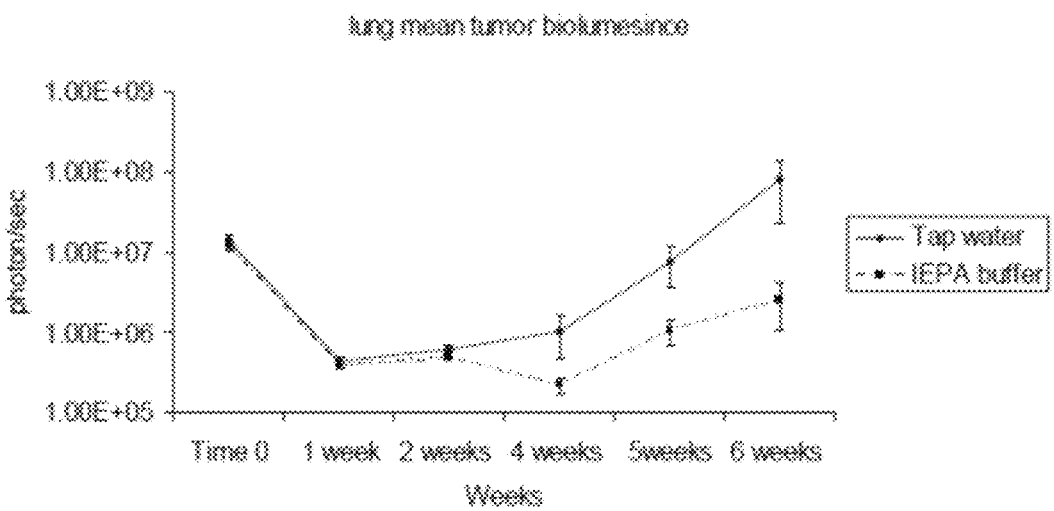

After failing first line treatment, the subject discontinued conventional therapy and began a self-administered course of vitamins, supplements, and approximately 60 grams of bicarbonate mixed in water daily. As of this submission, he has remained well, with stable tumor for 10 months. The subject's weight has remained stable. The subject walks 2 miles every day and had cataract surgery in March 2008 without complications. CT scans from Dec. 5, 2007 and Apr. 18, 2008 are shown in FIG. 9. These images are representative in that some of the liver lesions have increased in size, some have decreased, and some have remained stable. Interestingly, the tumors that were necrotic in the initial scan became much less so on the follow-up study. While little information can be gained from a single case report, it is noted that the subject has tolerated the "very high" bicarbonate administration used in the simulations without complication for nearly 1 year, suggesting that it is clinically feasible.

One key result of the simulations is that the use of buffers with a pKa of approximately 7 might yield to results similar, or better than, those obtained with bicarbonate (pKa 6.1 [Putnam R W, et al., Which value for the first dissociation constant of carbonic acid should be used in biological work? *Am J Physiol* 1991; 260(5 Pt 1):C1113-6]. Candidate buffers include cholamine chloride (pKa 7.1), N,N-Bis(2-hydroxyethyl)-2-aminoethanesulfonic acid ("BES"; pKa 7.15), N-Tris(hydroxymethyl)methyl-2-aminoethanesulfonic acid ("TES"; pKa 7.5) or 4-(2-Hydroxyethyl)piperazine-1-ethanesulfonic acid ("HEPES"; pKa 7.55) [Good N E, et al., Hydrogen ion buffers for biological research. *Biochemistry* 1966; 5(2):467-77]. However, the effect of these buffers in vivo must be evaluated because bicarbonate is a natural buffer controlled by the organism through ventilation and excretion in kidneys, whereas the use of an artificial buffer might lead to side effects and toxicity.

Thus, the experiments presented herein demonstrate that oral administration of clinically feasible amounts of $NaHCO_3$ may be sufficient to increase the acidic intratumoral and peri-tumoral pHe in small tumors. Furthermore, the consequent changes in the tumor-host dynamics may inhibit tumor growth and invasion. The results further demonstrate the utility of systemic administration of pH buffers as a novel cancer therapy.

All references cited in the present application are incorporated in their entirety herein by reference to the extent not inconsistent herewith.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of treating at least one cancerous tumor in a patient having at least one cancerous tumor comprising:
    administering 200 mM of 2-imidazole-1-yl-3-ethoxycarbonylpropionic acid (IEPA) to the patient wherein the IEPA is repeatedly and chronically orally administered;
    wherein administration of the IEPA increases intratumoral extracellular pH (pHe) in the at least one cancerous tumor of the patient above pre-administration pHe levels that were obtained prior to initiation of any treatment with the IEPA;
    wherein the increase in the intratumoral pHe of the at least one cancerous tumor treats the at least one cancerous tumor in the patient.

2. The method according to claim 1, further comprising administering at least one chemotherapeutic agent to the patient simultaneously with the administration of the IEPA.

3. The method according to claim 1, wherein the at least one cancerous tumor is selected from the group consisting of breast cancer, lung cancer, liver cancer, pancreatic cancer, prostate cancer, sarcomas, stomach cancer, testicular cancer, and ovarian cancer.

4. The method of claim 1, further comprising administering at least one chemotherapeutic agent to the patient at a time period prior to the initiation of a first administration of the IEPA.

5. A method of inhibiting metastasis of at least one cancer cell in a patient having at least one cancer cell comprising:
    administering 200 mM of 2-imidazole-1-yl-3-ethoxycarbonylpropionic acid (IEPA) to the patient wherein the IEPA is repeatedly and chronically orally administered;
    wherein administration of the IEPA increases intratumoral extracellular pH (pHe) in the at least one cancer cell of the patient above pre-administration pHe levels that were obtained prior to initiation of any treatment with the IEPA;
    wherein the increase in the intratumoral pHe of the at least one cancer cell inhibits metastasis of the at least one cancer cell in the patient.

6. The method of claim 5, further comprising administering at least one chemotherapeutic agent to the patient simultaneously with the administration of the IEPA.

7. The method according to claim 5, wherein the at least one cancer cell is selected from the group consisting of breast cancer cells, lung cancer cells, liver cancer cells, pancreatic cancer cells, prostate cancer cells, sarcomas, stomach cancer cells, testicular cancer cells, and ovarian cancer cells.

8. The method of claim 5, further comprising administering at least one chemotherapeutic agent to the patient at a time period prior to the initiation of a first administration of the IEPA.

* * * * *

UNITED STATES PATENT AND TRADEMARK OFFICE
CERTIFICATE OF CORRECTION

PATENT NO. : 10,258,607 B2
APPLICATION NO. : 13/479638
DATED : April 16, 2019
INVENTOR(S) : Robert J. Gillies et al.

It is certified that error appears in the above-identified patent and that said Letters Patent is hereby corrected as shown below:

In the Specification

Column 1, Line 16, please add:
STATEMENT OF GOVERNMENT INTEREST
This invention was made with government support under grant number CA193489 awarded by the National Institutes of Health. The Government has certain rights in the invention.

Signed and Sealed this
Fourteenth Day of May, 2019

Andrei Iancu
*Director of the United States Patent and Trademark Office*